United States Patent
Hubbard, Jr. et al.

(10) Patent No.: US 8,407,912 B2
(45) Date of Patent: Apr. 2, 2013

(54) SPRAY DRIED HUMAN PLASMA

(75) Inventors: Dennis Brian Hubbard, Jr., Lancaster, MA (US); Michael Haley, Marlboro, MA (US)

(73) Assignee: Velico Medical, Inc., Beverly, MA (US)

( * ) Notice: Subject to any disclaimer, the term of this patent is extended or adjusted under 35 U.S.C. 154(b) by 0 days.

(21) Appl. No.: 13/415,440

(22) Filed: Mar. 8, 2012

(65) Prior Publication Data
US 2012/0167405 A1   Jul. 5, 2012

Related U.S. Application Data

(63) Continuation of application No. PCT/US2010/049176, filed on Sep. 16, 2010.

(51) Int. Cl.
*F26B 11/00* (2006.01)
(52) U.S. Cl. .......................................... 34/82; 424/159.1
(58) Field of Classification Search ................ 34/77, 78, 34/82, 90; 424/159.1, 130.1
See application file for complete search history.

(56) References Cited

U.S. PATENT DOCUMENTS

| | | | |
|---|---|---|---|
| 2,411,152 A | 11/1946 | Folsom | |
| 2,528,476 A | 10/1950 | Roos et al. | |
| 3,228,838 A | 1/1966 | Rinfret et al. | |
| 3,230,689 A | 1/1966 | Hussmann | |
| 3,449,124 A | 6/1969 | Lipner | |
| 3,507,278 A | 4/1970 | Werding | |
| 3,644,128 A | 2/1972 | Lipner | |
| 3,654,705 A | 4/1972 | Smith et al. | |
| 4,187,617 A * | 2/1980 | Becker et al. | 34/576 |
| 4,251,510 A | 2/1981 | Tankersley | |
| 4,347,259 A | 8/1982 | Suzuki et al. | |
| 4,358,901 A | 11/1982 | Takabatake et al. | |
| 4,378,346 A | 3/1983 | Tankersley | |
| 4,787,154 A | 11/1988 | Titus | |
| 5,096,537 A * | 3/1992 | Bergquist et al. | 159/4.01 |
| 5,145,706 A | 9/1992 | Hagi et al. | |
| 5,252,221 A | 10/1993 | van Dommelen et al. | |
| 5,372,811 A | 12/1994 | Yoder | |
| 5,522,156 A | 6/1996 | Ware | |
| 5,562,919 A | 10/1996 | Doty et al. | |
| 5,575,999 A | 11/1996 | Yoder | |

(Continued)

FOREIGN PATENT DOCUMENTS

| | | |
|---|---|---|
| CA | 1182411 | 2/1985 |
| CA | 2065582 | 10/1992 |

(Continued)

OTHER PUBLICATIONS

Edwards et al.; The Preparation and Use of Dried Plasma for Transfusion; British Medical Journal; vol. 1, No. 4131; Mar. 9, 1940; pp. 377-381.

(Continued)

*Primary Examiner* — Stephen M. Gravini
(74) *Attorney, Agent, or Firm* — Pierce Atwood LLP; Joseph M. Maraia

(57) ABSTRACT

The technology relates to spray dried plasma and methods of making the same. The method includes providing plasma to a spray drying apparatus, spray drying the plasma, at the spray drying apparatus, to form physiologically active plasma powder, the spray drying apparatus configured utilizing one or more parameters, and storing the physiologically active plasma powder.

23 Claims, 33 Drawing Sheets

U.S. PATENT DOCUMENTS

| | | | |
|---|---|---|---|
| 5,581,903 A * | 12/1996 | Botich | 34/264 |
| 5,647,142 A * | 7/1997 | Andersen et al. | 34/373 |
| 5,727,333 A | 3/1998 | Folan | |
| 5,924,216 A * | 7/1999 | Takahashi | 34/374 |
| 5,993,804 A | 11/1999 | Read et al. | |
| 6,004,576 A | 12/1999 | Weaver et al. | |
| 6,148,536 A | 11/2000 | Lijima | |
| 6,308,434 B1 * | 10/2001 | Chickering et al. | 34/373 |
| 6,345,452 B1 | 2/2002 | Feuilloley et al. | |
| 6,463,675 B1 * | 10/2002 | Hansen et al. | 34/373 |
| 6,523,276 B1 | 2/2003 | Meldrum | |
| 6,526,774 B1 | 3/2003 | Lu et al. | |
| 6,560,897 B2 * | 5/2003 | Chickering et al. | 34/577 |
| 6,569,447 B2 | 5/2003 | Kisic et al. | |
| 6,582,654 B1 | 6/2003 | Kral et al. | |
| 6,723,497 B2 | 4/2004 | Wolkers et al. | |
| 7,007,406 B2 | 3/2006 | Wang et al. | |
| 7,089,681 B2 | 8/2006 | Herbert et al. | |
| 7,419,682 B2 | 9/2008 | Campbell et al. | |
| 7,527,805 B2 | 5/2009 | Crenshaw et al. | |
| 8,322,046 B2 | 12/2012 | Wang et al. | |
| 2002/0122803 A1 | 9/2002 | Kisic et al. | |
| 2002/0182195 A1 | 12/2002 | Marguerre et al. | |
| 2003/0037459 A1 | 2/2003 | Chickering, III et al. | |
| 2003/0099633 A1 | 5/2003 | Campbell et al. | |
| 2003/0103962 A1 | 6/2003 | Campbell et al. | |
| 2003/0143518 A1 | 7/2003 | Luck et al. | |
| 2003/0180283 A1 | 9/2003 | Batycky et al. | |
| 2003/0190314 A1 | 10/2003 | Campbell et al. | |
| 2004/0146565 A1 | 7/2004 | Strohbehn et al. | |
| 2004/0202660 A1 | 10/2004 | Campbell et al. | |
| 2005/0170068 A1 | 8/2005 | Roodink et al. | |
| 2005/0271674 A1 | 12/2005 | Campbell et al. | |
| 2006/0045907 A1 | 3/2006 | Campbell et al. | |
| 2006/0088642 A1 | 4/2006 | Boersen et al. | |
| 2006/0130768 A1 | 6/2006 | Crenshaw et al. | |
| 2006/0216687 A1 | 9/2006 | Alves-Filho et al. | |
| 2007/0014806 A1 | 1/2007 | Marguerre et al. | |
| 2008/0060213 A1 | 3/2008 | Gehrmann et al. | |
| 2008/0138340 A1 | 6/2008 | Campbell et al. | |
| 2008/0145444 A1 | 6/2008 | Merchant et al. | |
| 2008/0213263 A1 | 9/2008 | Campbell et al. | |
| 2009/0092678 A1 | 4/2009 | Marguerre et al. | |
| 2009/0155410 A1 | 6/2009 | Crenshaw et al. | |
| 2010/0215667 A1 | 8/2010 | Campbell et al. | |
| 2012/0167405 A1 * | 7/2012 | Hubbard et al. | 34/82 |

FOREIGN PATENT DOCUMENTS

| | | |
|---|---|---|
| CH | 622683 | 4/1981 |
| CN | 1315139 | 10/2001 |
| DE | 3507278 A1 | 9/1986 |
| EP | 0058903 | 9/1982 |
| EP | 1050220 A1 | 11/2000 |
| GB | 573500 | 11/1945 |
| GB | 886533 | 1/1962 |
| GB | 886533 | 10/1962 |
| GB | 964367 | 7/1964 |
| GB | 975786 | 11/1964 |
| GB | 1188168 | 4/1970 |
| GB | 2003042 | 3/1979 |
| JP | 56011903 | 2/1981 |
| JP | 63218201 | 9/1988 |
| JP | 01011618 | 1/1989 |
| JP | 03131302 | 6/1991 |
| JP | 03181301 | 8/1991 |
| JP | 05245301 A | 9/1993 |
| JP | 525910 | 10/1993 |
| JP | 5252910 | 10/1993 |
| JP | 10182124 | 7/1998 |
| JP | 2002009037 | 1/2002 |
| JP | 2005191275 | 7/2005 |
| JP | 2007216158 | 8/2007 |
| WO | 9615849 | 5/1996 |
| WO | 9618312 | 6/1996 |
| WO | 9738578 | 10/1997 |
| WO | 9907236 | 2/1999 |
| WO | 9907390 | 2/1999 |
| WO | 0056166 | 9/2000 |
| WO | 0172141 | 10/2001 |
| WO | 02078741 | 10/2002 |
| WO | 02078742 | 10/2002 |
| WO | 02/092213 | 11/2002 |
| WO | 03030654 | 4/2003 |
| WO | 03030918 | 4/2003 |
| WO | 03063607 | 8/2003 |
| WO | 2004075988 | 9/2004 |
| WO | 2007036227 | 4/2007 |
| WO | 2008/122288 | 10/2008 |
| WO | 2010117976 | 10/2010 |

OTHER PUBLICATIONS

Mini Spray Dryer B-290—Application Note; www.buchi.com; Mar. 30, 2008.
Nano Spray Dryer B-90; www.buchi.com; Jul. 18, 2011.
Mini Spray Dryer System Configuration; www.buchi.com; Jan. 8, 2007.
Quick Operation Guide; Mini Spray Dryer B-290; www.buchi.com; Sep. 16, 2004.
Process Parameters; www.buchi.com; Nov. 21, 2008.
Training Papers Spray Drying; Version B; www.buchi.com; 19 pages; Oct. 29, 2002.
Mini Spray Dryer B-290; www.buchi.com; May 10, 2007.
Operation Manual; Mini Spray Dryer B-290; Version G; www.buchi.com; Feb. 8, 2007.
PCT International Search Report and Written Opinion; PCT/US2010/049176; Nov. 4, 2010.
Edwards et al., The Preparation and Use of Dried Plasma for Transfusion; British Medical journal; vol. 1, No. 4131; Mar. 9, 1940; pp. 377-381.
PCT International Search Report from International Application No. PCT/US2011/058358, filed Oct. 28, 2011, mailed Jul. 4, 2012.
Civil Action Cover Sheet; *Entegrion, Inc. vs Velico Medical, Inc.*, dated Oct. 19, 2012.
Complaint including Exhibit A, B, and C; *Entegrion, Inc. vs Velico Medical, Inc.*, dated Oct. 19, 2012.
Answer, Affirmative Defenses, Counterclaims, Cross-Claims and Jury Demand, *Entergion, Inc. vs Velico Medical, Inc.*, dated Dec. 3, 2012.
Entegrion's Reply to Courterclaims; *Entergion, Inc. vs. Velico Medical, Inc*; Dated Jan. 14, 2013.
Entegrion's Motion to Dismiss Counts I, II, V, VI and XI of Velico Medical, Inc's Counterclaims and Memorandum in Support of Entegrion's Motion to Dismiss Counts I, II, V, VI, and XI of Velico Medical, Inc.'s Counterclaims; *Entegrion, Inc. vs Velico Medical, Inc*; Dated Jan. 14, 2013.

* cited by examiner

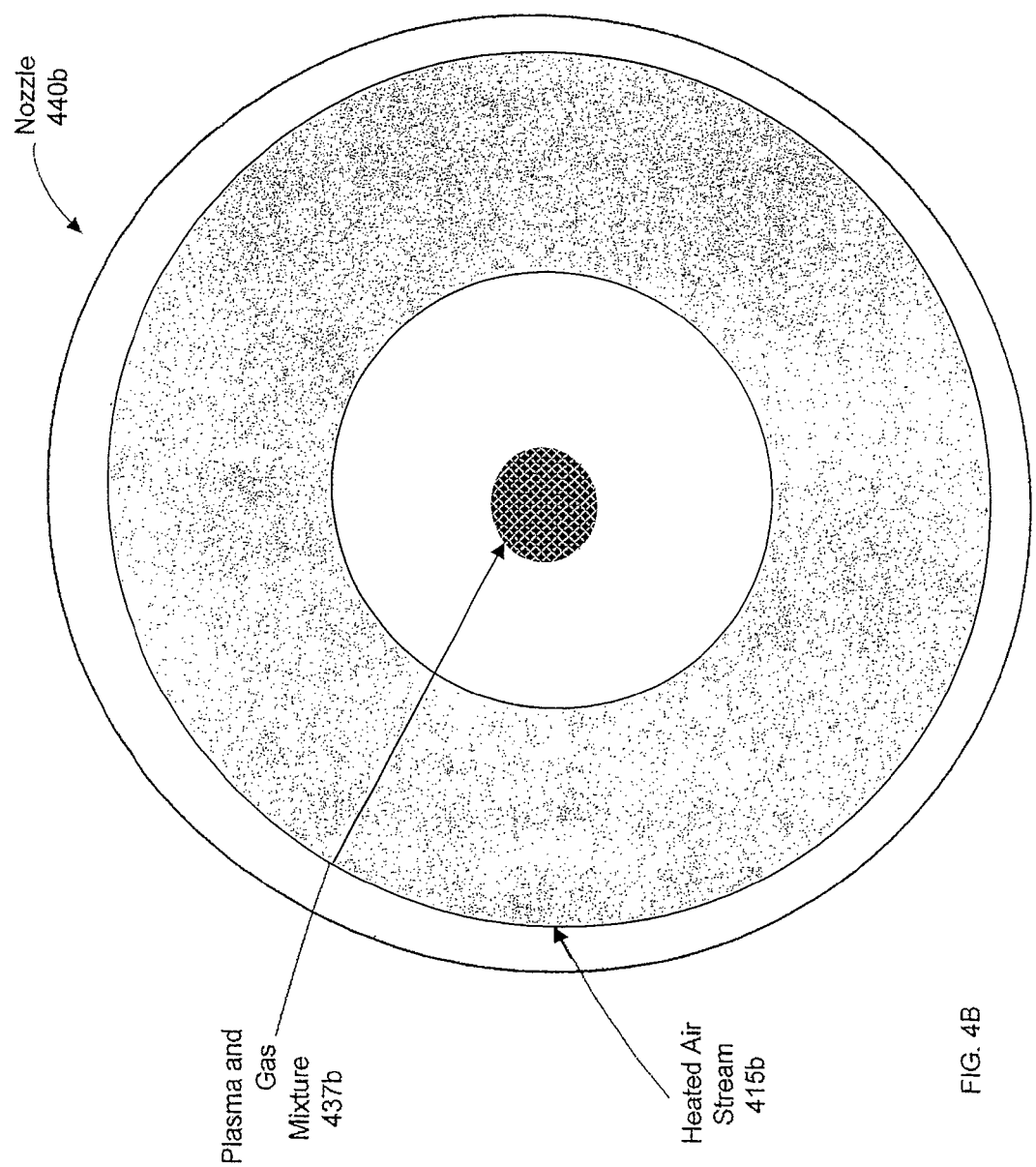

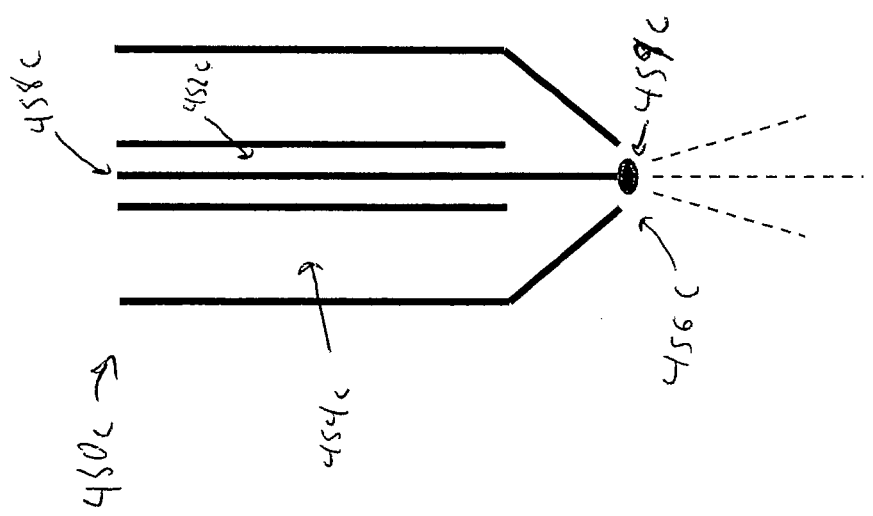

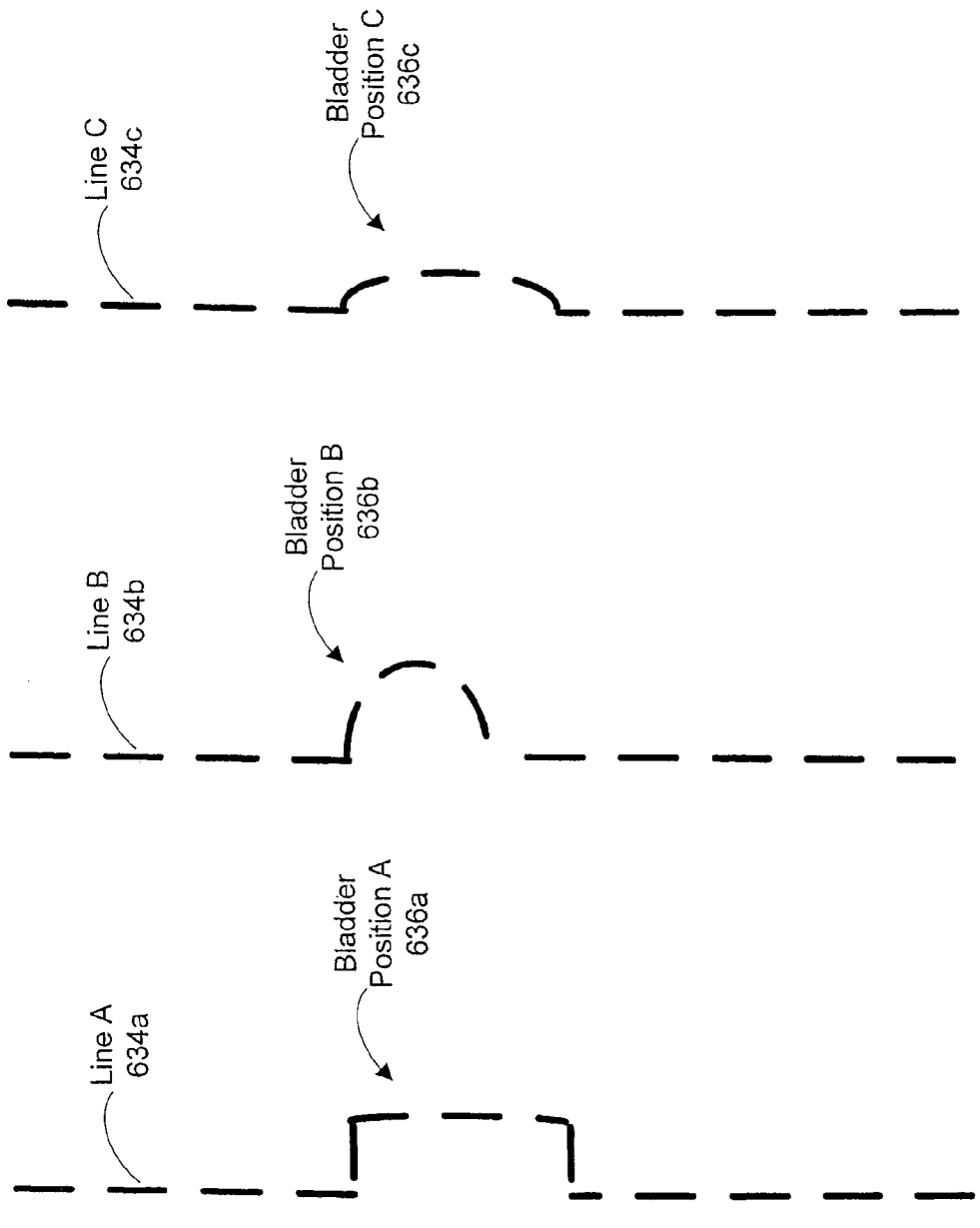

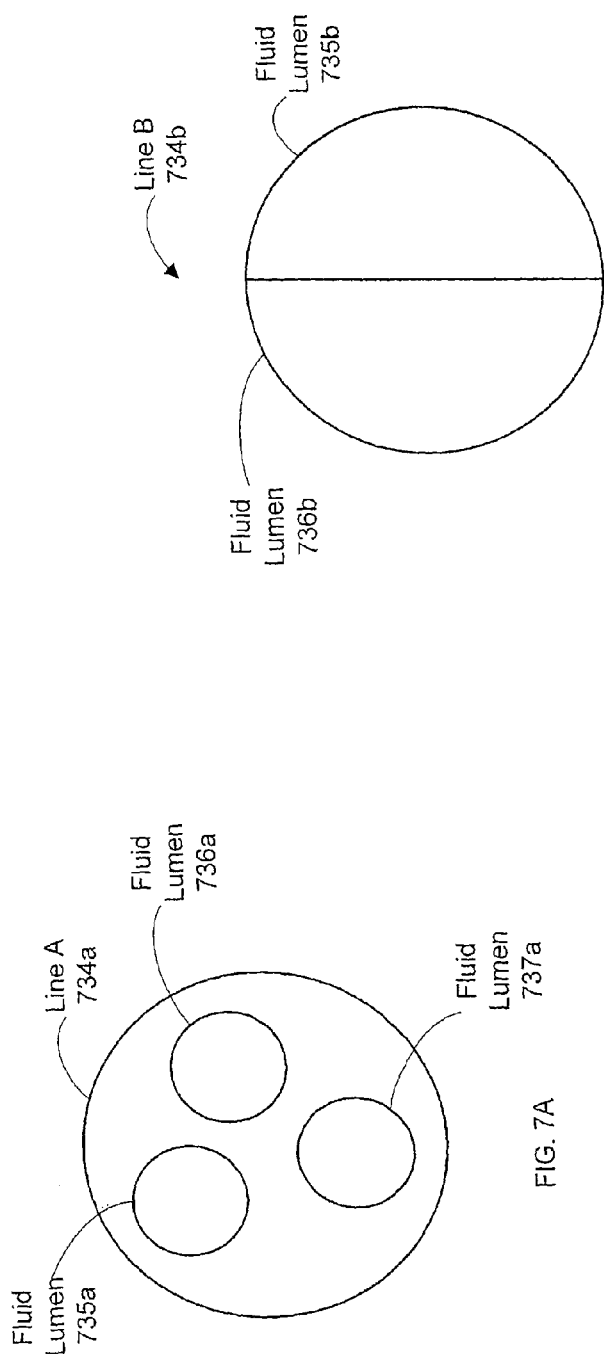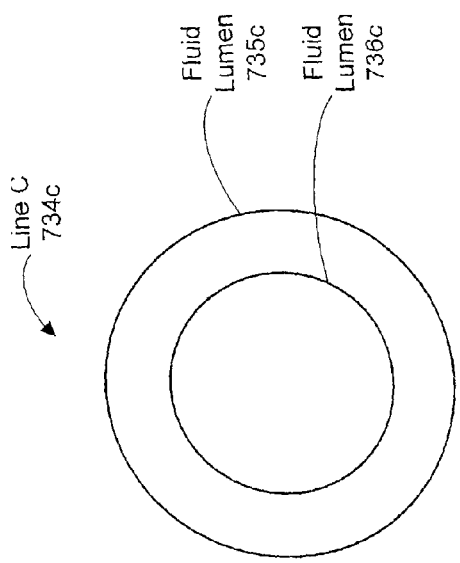

FIG. 9A

Integrated Storage and Reconstitution Device 900

Spray Dried Plasma Storage Device 950

Physiologically Active Plasma Powder 952

Sealing Mechanism 955

Reconstitution Device 957

Physiologically Active Reconstituted Plasma 990

Spray Dried Plasma Reconstitution Device 960

Reconstitution Fluid 965

```
┌──────────────────────┐
│  Warm-up Spray Drying│         1000
│      Apparatus       │
│        1005          │
└──────────┬───────────┘
           ↓
┌──────────────────────┐
│   Start Spray Drying │
│      Apparatus       │
│        1010          │
└──────────┬───────────┘
           ↓
┌──────────────────────┐
│  Provide Plasma to   │
│  Spray Drying Apparatus│
│        1020          │
└──────────┬───────────┘
           ↓
┌──────────────────────┐
│ Set Parameters for   │
│    Spray Drying      │
│        1030          │
└──────────┬───────────┘
           ↓
┌──────────────────────┐
│  Start Spray Drying  │
│        1040          │
└──────────┬───────────┘
           ↓
┌──────────────────────┐
│ Collect Physiologically│
│  Active Plasma Powder│
│        1050          │
└──────────────────────┘
```

- Attach Dehumidifier to Spray Drying Apparatus
  1110
- Attach Pre-dryer to Spray Drying Apparatus
  1115
- Attach Glassware to Spray Drying Apparatus
  1120
- Set Inlet Temperature to 107° C
  1125
- Set Pump Rate to 24%
  1130
- Set Aspiration to 100%
  1135
- Set Nitrogen Flow Rate to 35 mm Hg
  1140
- Start Spray Drying Process
  1145
- Monitor Outlet Temperature
  1150
  - Outside of 40° to 44° C → Adjust Pump Rate and/or Adjust Inlet Temperature
    1155
- Collect Physiologically Active Plasma Powder
  1160

FIG. 11

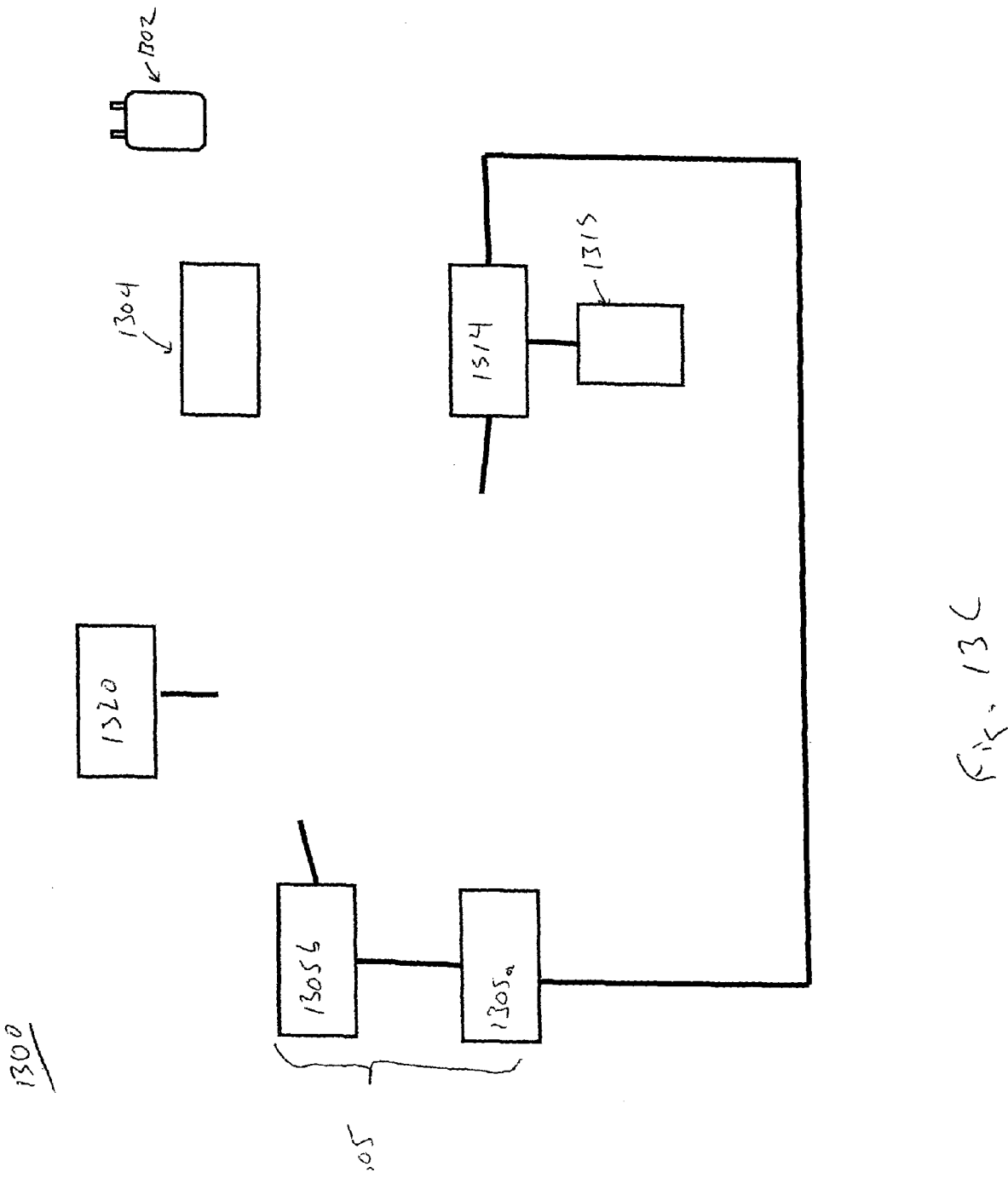

Coagulation Factor Activity of Thawed Plasma Derived from FFP*

| Coagulation Factor | Level† | | | | | Mean Change from Day 1 to Day 5 (%) | p Values |
|---|---|---|---|---|---|---|---|
| | Day 1 | Day 2 | Day 3 | Day 4 | Day 5 | | |
| Factor VIII (%) | | | | | | | |
| Blood group A | 107 ± 26 | 76 ± 19 | 66 ± 18 | 65 ± 17 | 63 ± 16 | 41 | <0.004‡ |
| Blood group B | 103 ± 44 | 74 ± 37 | 71 ± 35 | 67 ± 36 | 67 ± 33 | 35 | <0.02‡ |
| Blood group O | 70 ± 16 | 51 ± 10 | 43 ± 10 | 43 ± 7 | 41 ± 8 | 41 | <0.001‡ |
| Factor II (%) | 81 ± 9 | 81 ± 9 | 81 ± 9 | 80 ± 10 | 80 ± 10 | 1 | NS |
| Factor V (%) | 79 ± 7 | 75 ± 8 | 71 ± 9 | 68 ± 9 | 66 ± 9 | 16 | NS |
| Factor VII (%) | 90 ± 18 | 81 ± 15 | 76 ± 15 | 72 ± 14 | 72 ± 15 | 20 | NS |
| Factor X | 85 ± 13 | 84 ± 13 | 84 ± 15 | 82 ± 11 | 80 ± 11 | 6 | NS |
| Fibrinogen (mg/dL) | 225 ± 12 | 224 ± 13 | 224 ± 13 | 224 ± 17 | 225 ± 12 | 0 | NS |

Fig. 15

Characterization of Reconstituted Spray Dried Plasma

| Settings | | Samples Tested | | Stago Test Results | | | | | | | | | |
|---|---|---|---|---|---|---|---|---|---|---|---|---|---|
| Inlet Temp | Feed Pump Setting | | | PT (sec) | aPTT (sec) | FNG (mg/dL) | F-5 (IU/dL) | F-7 (IU/dL) | F-8 (IU/dL) | F-9 (IU/dL) | PC Clot (IU/dL) | PS Clot (IU/dL) |
| 97 C | 7% | 6 For PT, aPTT, FNG 1-2 For Factors and PS/PC | Average | 27.5 | 46.6 | 186.8 | 73.0 | 96.5 | 68.0 | 121.0 | 128.0 | 93.0 |
| | | | Min | 14.1 | 28.1 | 64.0 | 38.0 | 82.0 | 49.0 | 106.0 | 128.0 | 88.0 |
| | | | Max | 48.0 | 96.7 | 258.0 | 108.0 | 111.0 | 87.0 | 136.0 | 128.0 | 98.0 |
| 97 C | Variable | 1 For PT, aPTT, FIB 2 for PS/PC (Minimum 6 for Factors) | Average | 22.5 | 46.4 | 216.3 | 43.0 | 60.0 | 42.5 | 66.8 | 92.5 | 66.0 |
| | | | Min | 19.2 | 37.2 | 109.0 | 17.0 | 40.0 | 23.0 | 49.0 | 89.0 | 64.0 |
| | | | Max | 26.7 | 66.0 | 273.0 | 65.0 | 86.0 | 85.0 | 78.0 | 96.0 | 68.0 |
| 112 C | Variable | 34 7 for PS/PC | Average | 25.8 | 50.2 | 197.6 | 49.6 | 68.0 | 39.3 | 63.9 | 86.5 | 79.8 |
| | | | Min | 20.2 | 36.6 | 121.0 | 27.0 | 33.0 | 10.0 | 7.0 | 54.0 | 66.0 |
| | | | Max | 42.2 | 97.1 | 292.0 | 73.0 | 93.0 | 89.0 | 107.0 | 104.0 | 111.0 |
| 117 C | Variable | Minimum 10 For PT, aPTT, FIB 2 for PS/PC Minimum 10 For Factors | Average | 27.3 | 56.5 | 187.2 | 41.8 | 72.5 | 32.3 | 65.3 | 88.3 | 63.3 |
| | | | Min | 21.9 | 48.7 | 129.0 | 31.0 | 31.0 | 9.0 | 13.0 | 59.0 | 56.0 |
| | | | Max | 30.8 | 63.8 | 273.0 | 59.0 | 110.0 | 65.0 | 109.0 | 107.0 | 69.0 |

FIG. 17A

Characterization of Reconstituted Spray Dried Plasma

| Batch | | Name | PT+ 10 (sec.) | aPTT (sec.) | FNG (mg/dL) | F-5 (IU/dL) | F-7 (IU/dL) | F-8 (IU/dL) | F-9 (IU/dL) |
|---|---|---|---|---|---|---|---|---|---|
| 2010-040 | 1 | 2010-040GLY | 17.2 | 41.6 | 259 | 93 | 81 | 96 | 108 |
| 2010-040 | 1 | 2010-040-GLY | 14.4 | 40.2 | 281 | 107 | 95 | 14 | 16 |
| 2010-041 | 1 | 2010-041GLY | 16.3 | 39.9 | 271 | 93 | 84 | 98 | 118 |
| 2010-072 | 1 | 2010-072GLY | 14.4 | 34.7 | 277 | 105 | 80 | 46 | 116 |
| 2010-074 | 1 | 2010-074GLY | 13.8 | 30.5 | 346 | 63 | 85 | 88 | 106 |
| 2010-077 | 1 | 2010-077GLY | 15.9 | 32.2 | 360 | 88 | 64 | 84 | 96 |
| 2010-079 | 1 | 2010-079GLY | 14.4 | 36.3 | 259 | 83 | 86 | 44 | 79 |
| 2010-081 | 1 | 2010-081GLY | 15.4 | 35.1 | 243 | 82 | 82 | 64 | 92 |
| 2010-083 | 1 | 2010-083GLY | 16.1 | 39.1 | 267 | 60 | 96 | 36 | 108 |
| 2010-102 | 1 | 2010-102GLY | 15.4 | 36.2 | 283 | 71 | 44 | 42 | 55 |
| 2010-104 | 1 | 2010-104GLY | 16.0 | 34.6 | 235 | 53 | 39 | 40 | 83 |
| | | Average | 15 | 36 | 280 | 82 | 76 | 59 | 89 |
| | | Min | 14 | 31 | 235 | 53 | 39 | 14 | 16 |
| | | Max | 17 | 42 | 360 | 107 | 96 | 98 | 118 |

FIG. 17B

SPRAY DRIED HUMAN PLASMA

CROSS REFERENCE TO RELATED APPLICATION

This application is a continuation of PCT/US2010/049176 filed Sep. 16, 2010, entitled, "Spray Dried Human Plasma", the entire contents of which are incorporated herein by reference.

FIELD OF THE INVENTION

The present invention relates generally to methods and apparatus for producing and/or using spray dried human plasma.

BACKGROUND

Blood plasma is the yellow liquid component of blood, in which the blood cells of whole blood would normally be suspended. Blood plasma makes up about 55% of the total blood volume. Blood plasma is mostly water (e.g., 90% by volume) and contains dissolved proteins, glucose, clotting factors, mineral ions, hormones, and/or carbon dioxide. Blood plasma is prepared by spinning a tube of fresh blood in a centrifuge until the blood cells fall to the bottom of the tube. The blood plasma is then poured or drawn off. Blood plasma is frequently frozen fresh for future uses. Although frozen plasma is the current standard of care, there are numerous problems with this technology. For example, the bag containing the frozen plasma become brittle and often gets damaged during storage or transportation. Maintaining frozen plasma at the appropriate temperature during storage and transportation is very expensive. It requires mechanical freezers to keep the frozen plasma at −18° C. or lower. Shipping requires special shipping containers to maintain the frozen state and reduce breakage of the bag. Use of the frozen plasma is delayed by 30-45 minutes due to the thawing time. Moreover, the preparation for use requires trained staff and specialized thawing device in a regulated laboratory. Finally, fresh frozen plasma has a limited shelf life of 12 months at −18° C. Once thawed, the frozen plasma must be used within 24 hours.

In an attempt to avoid the disadvantages of frozen plasma, some have freeze dried (i.e., lyophilized) plasma. However, the freeze drying process produces a product composed of large, irregular sized grains or particles. Such products can be difficult or impossible to reconstitute to a form suitable for administration to a patient. Furthermore, the freeze drying process requires transfer of the product from the lyophyilizer to the final container, thus requiring post-processing sterility testing. The freeze drying process can only be done in batch mode; continuous processing is not possible with freeze drying. Moreover, manufacturing scale-up requires changes to the freeze drying process, and there are protein recovery issues at scale-up.

Accordingly, a need still exists in the field for plasma that may be stored in a wide range of environments without freezers or refrigerators, be available for use by first responders at the initial point of care, and can be transfused in minutes without the 30-45 minute delay associated with thawing of frozen plasma.

SUMMARY OF THE INVENTION

The present invention provides an extracorporeal sterile, closed plasma processing system, which can be used to produce a spray dried, physiologically active plasma powder product that has a long storage life at room temperature; that can easily be stored and shipped; that is versatile, durable and simple, and that can be easily and rapidly reconstituted and used at the point of care. The processing system of the present invention can produce spray dried plasma in either a batch (single unit) or a continuous (pooled units) process mode. The resulting plasma powder can be dried directly into the final, attached sterile container, which can later be rapidly and easily reconstituted to produce transfusion grade plasma. The spray dried powder can be stored at least 2-3 years at virtually any temperature (e.g., −180° C. to 50° C.). The costs associated with storage and shipping of the spray dried powder are significantly lower, because of its lighter weight and broader range of temperature tolerance compared to frozen plasma. At the point of care, the spray dried powder is rapidly reconstituted (30-120 seconds), avoiding the need for special equipment and trained staff. In contrast to frozen plasma, which takes 30-45 minutes to thaw and must be used within 24 hours, the spray dried plasma of the present invention avoids waste since the caregiver can rapidly prepares the amount of plasma required for a given patient, rather than trying to assess and predict the amount of plasma required and thawing sufficient plasma to meet this anticipated need.

One approach to spray dried human plasma is a method that includes providing plasma to a spray drying apparatus; spray drying the plasma, at the spray drying apparatus, to form physiologically active plasma powder, the spray drying apparatus configured utilizing one or more parameters; and storing the physiologically active plasma powder.

Another approach to spray dried human plasma is a spray drying apparatus. The spray drying apparatus includes a pump device configured to transport plasma from a liquid plasma storage device at a pump rate; a heated air stream device configured to deliver an air stream at an inlet temperature; a non reactive gas supply device configured to supply a non reactive gas at a flow rate; a spray nozzle configured to spray the plasma into a spray chamber utilizing the non reactive gas and the air stream; and a particle collection device configured to collect the sprayed dried plasma via a vacuum formed by a vacuum pump at an aspiration setting.

Another approach to spray dried human plasma is a method. The method includes providing a physiologically active plasma powder; providing a reconstitution fluid; and reconstituting physiologically active reconstituted plasma by mixing the physiologically active plasma powder and the reconstitution fluid.

Another approach to spray dried human plasma is a method. The method includes providing, from a non reactive gas supply to a spray nozzle, a non reactive gas at a flow rate; providing, from a dehumidifier to the spray nozzle, a heated air stream at an inlet temperature; providing, from a pump device to the spray nozzle, plasma at a pump setting; spraying, at the spray nozzle, the non reactive gas, the heated air stream, and the plasma into a spray chamber to form a physiologically active plasma powder, the heated air stream enabling transfer of moisture from the plasma to the heated air stream.

Another approach to spray dried human plasma is a spray dried physiologically active plasma powder. The spray dried physiologically active plasma powder is prepared by providing plasma to a spray drying apparatus; and spray drying, at the spray drying apparatus, the plasma to form the physiologically active plasma powder, the spray drying apparatus configured utilizing one or more parameters.

Another approach to spray dried human plasma is a physiologically active reconstituted plasma. The physiologically active reconstituted plasma is prepared by providing plasma to a spray drying apparatus; spray drying, at the spray drying apparatus, the plasma to form physiologically active plasma powder, the spray drying apparatus configured utilizing one or more parameters; and reconstituting the physiologically active plasma powder utilizing a reconstitution fluid to form the physiologically active reconstituted plasma.

As mentioned above, the processing systems of the type described herein can be used to produce spray dried physiologically active plasma powder in either a batch (single unit) or a continuous (pooled units) process mode.

One approach to spray dried human plasma is a method that starts with one unit of plasma and produces spray dried physiologically active plasma powder from that same unit of plasma. One advantage of this approach is that it allows the coding of the plasma unit, which permits tracking and removal of a particular plasma unit from circulation if an issue (e.g., infection, contamination) is subsequently identified with the original donor.

Another approach to spray dried human plasma is a method that starts with two or more single units of plasma and produces a pooled spray dried physiologically active plasma powder from these specific units of plasma. In addition to the ability to track the resulting product, another advantage of this approach is that the pooled powder can be reconstituted in a smaller volume to produce a high potency plasma unit. For example, if two units of plasma are spray dried and later reconstituted in one volume of reconstitution fluid, the resulting plasma would contain twice the concentration of physiologically active proteins, clotting factors, etc.

Yet another approach to spray dried human plasma is a method that starts with a pooled source of plasma containing two or more pooled single units of plasma and produces a series of single units of spray dried physiologically active plasma powder. This approach offers the efficiency advantages of a continuous processing mode to produce numerous single units of spray dried physiologically active plasma powder.

Yet another approach to spray dried human plasma is a method that starts with a pooled source of plasma containing two or more pooled single units of plasma and produces a pooled amount of spray dried physiologically active plasma powder. This approach offers the efficiency advantages of a continuous processing mode. This approach could be used, for example, to produce larger amounts of spray dried physiologically active plasma powder to be applied directly to an open wound.

In other embodiments, any of the approaches above can include one or more of the following features.

In one aspect, a method is disclosed for spray drying plasma, the method including: providing plasma to a spray drying apparatus; spray drying, at the spray drying apparatus, the plasma to form physiologically active plasma powder; and storing the physiologically active plasma powder.

Some embodiments include, during the providing, spray drying, and storing steps, maintaining the plasma and plasma powder in an isolated sterile environment. Some embodiments include, processing plasma in a closed sterile process to produce physiologically active plasma powder suitable for reconstitution and transfusion to a human subject.

Some embodiments include, during the spray drying, maintaining the plasma at a temperature below a threshold temperature to prevent denaturing of proteins in the plasma. In some embodiments, the threshold temperature is 44° C. or less. In some embodiments, the threshold temperature is 48° C. or less. In some embodiments, the threshold temperature is 50° C. or less.

Some embodiments include, during the spray drying, maintaining the plasma at a temperature within a selected temperature range. Some embodiments include during the spray drying, maintaining the plasma at a temperature within a selected temperature range of 41-43° C. or 37-48° C.

In some embodiments, spray drying the plasma includes: directing plasma to a spray nozzle at a plasma flow rate; directing a heated drying gas to a drying chamber at an inlet temperature and a drying gas flow rate; directing a non reactive spray gas to the nozzle at a spray gas flow rate; combing the plasma and spray gas at the nozzle to atomize the plasma and dry the plasma; and combining the atomized plasma and drying gas to dry the atomized plasma.

In some embodiments, the inlet temperature is in the range of 85-120° C. or 92-117° C.

In some embodiments, the plasma flow rate is in the range of 2-20 mL/minute, 2-30 mL/min, 2-50 mL/min, etc. In some embodiments, the drying gas flow rate is in the range of 20-80 $m^3$/hour. In some embodiments, the spray gas flow rate is in the range of 300-500 L/hr.

In some embodiments, the plasma flow rate is in the range of 8-12 mL/minute. In some embodiments, the drying gas flow rate is in the range of 30-40 $m^3$/hour. In some embodiments, and the spray gas flow rate is in the range of 350-450 L/hr.

Some embodiments include determining an outlet temperature of the plasma powder; and adjusting at least one of: the plasma flow rate, the inlet temperature, the spray gas flow rate, and the drying gas flow rate based on the outlet temperature.

Some embodiments include reconstituting the physiologically active plasma powder utilizing a reconstitution fluid to form physiologically active reconstituted plasma.

Some embodiments include applying the physiologically active reconstituted plasma to a human. In some embodiments, the reconstitution fluid includes at least one selected from the list consisting of: distilled water, saline solution, and glycine. In some embodiments, the reconstitution fluid is a buffered solution.

In some embodiments, the powder, when reconstituted, exhibits physiological activity substantially equivalent to Thawed Plasma, Liquid Plasma, FP24, or FFP.

In some embodiments, the dried plasma, when reconstituted, is characterized by an aPTT of about 65 seconds or less, a PT of about 31 seconds or less, and a Fibrinogen level of at least about 100 mg/dL.

In some embodiments, the dried plasma, when reconstituted, is characterized by an aPTT of about 35 seconds or less, a PT of about 15 seconds or less, and a Fibrinogen level of at least about 223 mg/dL.

In some embodiments, the dried plasma, when reconstituted, is characterized by an aPTT in the range of 28-66 seconds, a PT in the range of 14-31 seconds, and a Fibrinogen level in the range of 100-300 mg/dL.

In some embodiments, the dried plasma, when reconstituted, is characterized by an aPTT in the range of 30-35 seconds, a PT in the range of 10-15 seconds, and a Fibrinogen level in the range of 223-500 mg/dL.

In some embodiments, the dried plasma, when reconstituted, is characterized by at least one of: a Factor VII level of at least about 10 IU/dL, a Factor IX level of at least about 10 IU/dL, a Protein C level of at least about 10 IU/dL, and a Protein S level of at least about 10 IU/dL.

In some embodiments, the dried plasma, when reconstituted, is characterized by at least one of: a Factor VII level of at least about 30 IU/dL, a Factor IX level of at least about 25

IU/dL, a Protein C level of at least about 55 IU/dL, and a Protein S level of at least about 54 IU/dL In some embodiments, the dried plasma, when reconstituted, is characterized by at least one of: a Factor VII level of at least about 54 IU/dL, a Factor IX level of at least about 70 IU/dL, a Protein C level of at least about 74 IU/dL, and a Protein S level of at least about 61 IU/dL.

In some embodiments, the dried plasma, when reconstituted, is characterized by at least one of: a Factor VII level in the range of 30-110 IU/dL, a Factor IX level in the range of 25-135 IU/dL, a Protein C level in the range of 55-130 IU/dL, and a Protein S level of in the range of 55-110 IU/dL.

In some embodiments, the dried plasma, when reconstituted, is characterized by at least one of: a Factor VII level in the range of 34-172 IU/dL, a Factor IX level in the range of 70-141 IU/dL, a Protein C level in the range of 74-154 IU/dL, and a Protein S level of in the range of 61-138 IU/dL.

In some embodiments, the dried plasma, when reconstituted, is characterized by at least one of: a Factor V level of at least about 10 IU/dL, and a Factor VIII level of at least about 10 IU/dL.

In some embodiments, the dried plasma, when reconstituted, is characterized by at least one of: a Factor V level of at least about 30 IU/dL, and a Factor VIII level of at least about 25 IU/dL.

In some embodiments, the dried plasma, when reconstituted, is characterized by at least one of: a Factor V level of at least about 63 IU/dL, and a Factor VIII level of at least about 47 IU/dL.

In some embodiments, the dried plasma, when reconstituted, is characterized by at least one of a Factor V level in the range of 63-135 IU/dL, a Factor VIII level in the range of 47-195 IU/dL.

In some embodiments, the powder has an average particle size of about 30 microns or less. In some embodiments, e the powder has a maximum particle size of about 100 microns or less.

In some embodiments, the powder includes at least 30% dried protein by weight.

In some embodiments, when reconstituted with 1 mL of fluid per 0.09 grams of powder, the reconstituted plasma has a protein concentration in the range of 35 mg/mL to 60 mg/mL.

In another aspect, a product is disclosed including: a physiologically active dried plasma in the form of a powder. In some embodiments, the physiologically active dried plasma is sterile.

In some embodiments, the powder, when reconstituted, exhibits physiological activity substantially equivalent to Thawed Plasma, Liquid Plasma, FP24, or FFP.

In some embodiments, the dried plasma, when reconstituted, is characterized by an aPTT of about 65 seconds or less, a PT of about 31 seconds or less, and a Fibrinogen level of at least about 100 mg/dL.

In some embodiments, the dried plasma, when reconstituted, is characterized by an aPTT of about 35 seconds or less, a PT of about 15 seconds or less, and a Fibrinogen level of at least about 223 mg/dL.

In some embodiments, the dried plasma, when reconstituted, is characterized by an aPTT in the range of 28-66 seconds, a PT in the range of 14-31 seconds, and a Fibrinogen level in the range of 100-300 mg/dL.

In some embodiments, the dried plasma, when reconstituted, is characterized by an aPTT in the range of 30-35 seconds, a PT in the range of 10-15 seconds, and a Fibrinogen level in the range of 223-500 mg/dL.

In some embodiments, the dried plasma, when reconstituted, is characterized by at least one of: a Factor VII level of at least about 10 IU/dL, a Factor IX level of at least about 10 IU/dL, a Protein C level of at least about 10 IU/dL, and a Protein S level of at least about 10 IU/dL.

In some embodiments, the dried plasma, when reconstituted, is characterized by at least one of: a Factor VII level of at least about 30 IU/dL, a Factor IX level of at least about 25 IU/dL, a Protein C level of at least about 55 IU/dL, and a Protein S level of at least about 54 IU/dL In some embodiments, the dried plasma, when reconstituted, is characterized by at least one of: a Factor VII level of at least about 54 IU/dL, a Factor IX level of at least about 70 IU/dL, a Protein C level of at least about 74 IU/dL, and a Protein S level of at least about 61 IU/dL.

In some embodiments, the dried plasma, when reconstituted, is characterized by at least one of: a Factor VII level in the range of 30-110 IU/dL, a Factor IX level in the range of 25-135 IU/dL, a Protein C level in the range of 55-130 IU/dL, and a Protein S level of in the range of 55-110 IU/dL.

In some embodiments, the dried plasma, when reconstituted, is characterized by at least one of: a Factor VII level in the range of 34-172 IU/dL, a Factor IX level in the range of 70-141 IU/dL, a Protein C level in the range of 74-154 IU/dL, and a Protein S level of in the range of 61-138 IU/dL.

In some embodiments, the dried plasma, when reconstituted, is characterized by at least one of: a Factor V level of at least about 10 IU/dL, and a Factor VIII level of at least about 10 IU/dL.

In some embodiments, the dried plasma, when reconstituted, is characterized by at least one of: a Factor V level of at least about 30 IU/dL, and a Factor VIII level of at least about 25 IU/dL.

In some embodiments, the dried plasma, when reconstituted, is characterized by at least one of: a Factor V level of at least about 63 IU/dL, and a Factor VIII level of at least about 47 IU/dL.

In some embodiments, the dried plasma, when reconstituted, is characterized by at least one of a Factor V level in the range of 63-135 IU/dL, a Factor VIII level in the range of 47-195 IU/dL.

In some embodiments, the powder has an average particle size of about 30 microns or less. In some embodiments, e the powder has a maximum particle size of about 100 microns or less.

In some embodiments, the powder includes at least 30% dried protein by weight.

In some embodiments, when reconstituted with 1 mL of fluid per 0.09 grams of powder, the reconstituted plasma has a protein concentration in the range of 35 mg/mL to 60 mg/mL.

In another aspect, an apparatus is disclosed for spray drying plasma including: a plasma source; a pressurized spray gas source; a drying gas source; a spray dry nozzle in sterile fluid communication with the plasma and spray gas sources; a drying chamber in fluid communication with the spray dry nozzle and the drying gas source to receive a spray of plasma from the nozzle for drying; a particle collection device configured to collect spray dried plasma from an outlet of the drying chamber; and a collection device gas outlet port in sterile fluid communication with the collection device, the gas outlet port including a sterile outlet port. In some embodiments, the spray nozzle, drying chamber, and collection device define a sterile isolated interior volume.

In some embodiments, the gas outlet port includes a sterile filter.

In some embodiments, the nozzle is in sterile fluid communication with each of the spray gas source and the drying gas source through a respective sterile filter.

In some embodiments, the gas outlet port is in fluid communication with an external volume through the sterile outlet filter.

In some embodiments, the gas outlet port is in fluid communication with the drying gas source to provide closed recirculation of the drying gas.

In some embodiments, the plasma source includes a peristaltic pump configured to deliver a flow of plasma to an inlet of the nozzle at a plasma flow rate.

In some embodiments, the spray gas source includes a source of pressurized non reactive gas, and is configured to deliver the non reactive gas to the nozzle at a spray gas flow rate.

In some embodiments, the drying gas source includes a source of drying gas, and is configured to deliver heated drying gas to the nozzle at a drying gas flow rate and an inlet temperature.

Some embodiments include a controller configured to control at least one selected from the list consisting of: the plasma flow rate, the spray gas flow rate, the drying gas flow rate, and the inlet temperature.

In some embodiments, at least one sensor for measuring outlet temperature information indicative of an outlet temperature the spray dried plasma, the sensor in communication with the controller. In some embodiments, the controller includes a servo loop that controls the outlet temperature to a selected value by adjusting, based on the outlet temperature information, at least one selected from the list consisting of: the plasma flow rate, the spray gas flow rate, the drying gas flow rate, and the inlet temperature. In some embodiments, the controller includes a servo loop that controls the outlet temperature to a selected value by adjusting, based on the outlet temperature information, the plasma flow rate.

In another aspect, an attachment for plasma spray drying apparatus including: a plasma inlet port for sterile attachment to a plasma source; a spray gas inlet port for removable sterile attachment to a pressurized gas source; at least one drying gas inlet port for removable sterile attachment to a drying gas source; a spray dry nozzle in fluid communication with the plasma and spray gas inlets; a drying chamber in fluid communication with the attached spray nozzle and drying gas inlet to receive a spray of plasma for drying; a particle collection device configured to collect spray dried plasma from an outlet of the drying chamber; and a collection device gas outlet port in sterile fluid communication with the collection device. In some embodiments, the spray nozzle, drying chamber, and collection device define a sterile isolated interior volume.

In some embodiments, at least one of the inlet and outlet ports includes a sterile filter.

In some embodiments, the drying chamber is at least partially collapsible.

In some embodiments, the attachment includes a plastic or polymer material.

In some embodiments, the particle collection device includes a cyclone chamber.

In some embodiments, the particle collection device includes a detachable storage portion configured to receive collected spray dried plasma.

In another aspect, a product is disclosed including: a physiologically active spray dried plasma powder made using the methods described herein, e.g., the method described above.

Various embodiments may include any of the above described features, techniques, elements, etc., either alone, or in any suitable combination.

The plasma spray drying techniques described herein can provide one or more of the following advantages. An advantage to the plasma spray drying techniques described herein is that the plasma is not overheated during the spray drying process, which increases the recovery rate of physiologically functional plasma proteins, thereby increasing the efficacy of the plasma powder. Another advantage to the plasma spray drying techniques described herein is that the plasma can be stored for future use without refrigeration, thereby extending the shelf life and potential uses of the plasma (e.g., on the battlefield, in space, at sea, etc.). An additional advantage to the plasma spray drying techniques described herein is that the process parameters are controlled by the output temperature thereby enabling the quantity of processed plasma to be scaled by monitoring the output temperature and adjusting the pump rate and/or the inlet temperature accordingly to meet the required output temperature for the spray dried plasma.

Other aspects and advantages of the present invention will become apparent from the following detailed description, taken in conjunction with the accompanying drawings, illustrating the principles of the invention by way of example only.

BRIEF DESCRIPTION OF THE DRAWINGS

The foregoing and other objects, features, and advantages of the present invention, as well as the invention itself, will be more fully understood from the following description of various embodiments, when read together with the accompanying drawings.

FIGS. 1A-1B are diagrams of exemplary spray drying systems;

FIG. 2 is a diagram of another exemplary spray drying system;

FIG. 3A is a diagram of another exemplary spray drying system;

FIG. 3B is an illustration of a cyclone chamber;

FIGS. 4A-4C are diagrams of exemplary spray nozzles;

FIGS. 5A-5B are diagrams of other exemplary centrifuge systems;

FIGS. 6A-6C are diagrams of exemplary bladder positions for centrifuge devices;

FIGS. 7A-7C are diagrams of exemplary lines for centrifuge devices;

FIG. 8A is a diagram of an exemplary spray dried plasma reconstitution device;

FIG. 8B is a diagram of an exemplary spray dried plasma storage bag;

FIG. 9A is a diagram of an exemplary integrated storage and reconstitution device;

FIG. 9B is a diagram of an exemplary integrated storage and reconstitution device;

FIG. 10 is a flowchart depicting an exemplary spray drying process for plasma;

FIG. 11 is a flowchart depicting another exemplary spray drying process for plasma;

FIG. 12 is a flowchart depicting an exemplary process of applying physiologically active reconstituted plasma to a human patient;

FIG. 13A-13C are diagrams of another exemplary spray drying system;

FIGS. 13D-13F are diagrams of an attachment to a spray drying system;

FIGS. 14A-D are illustrations of air flow configurations for various spray drying systems;

FIG. 15 is a chart illustrating the physiological activity of fresh frozen plasma, with the following symbol definitions: *from Downes et al. "*Serial measurement of clotting factors in thawed plasma for five days.*" Transfusion 2001; 41:570; †Mean±SD; ‡(Comparison of Factor VIII activity at Day 1 and that at Day 3 was statistically significant;

FIGS. 17A-17B are charts illustrating the results of tests on spray dried plasma.

DETAILED DESCRIPTION

Figure 1A:
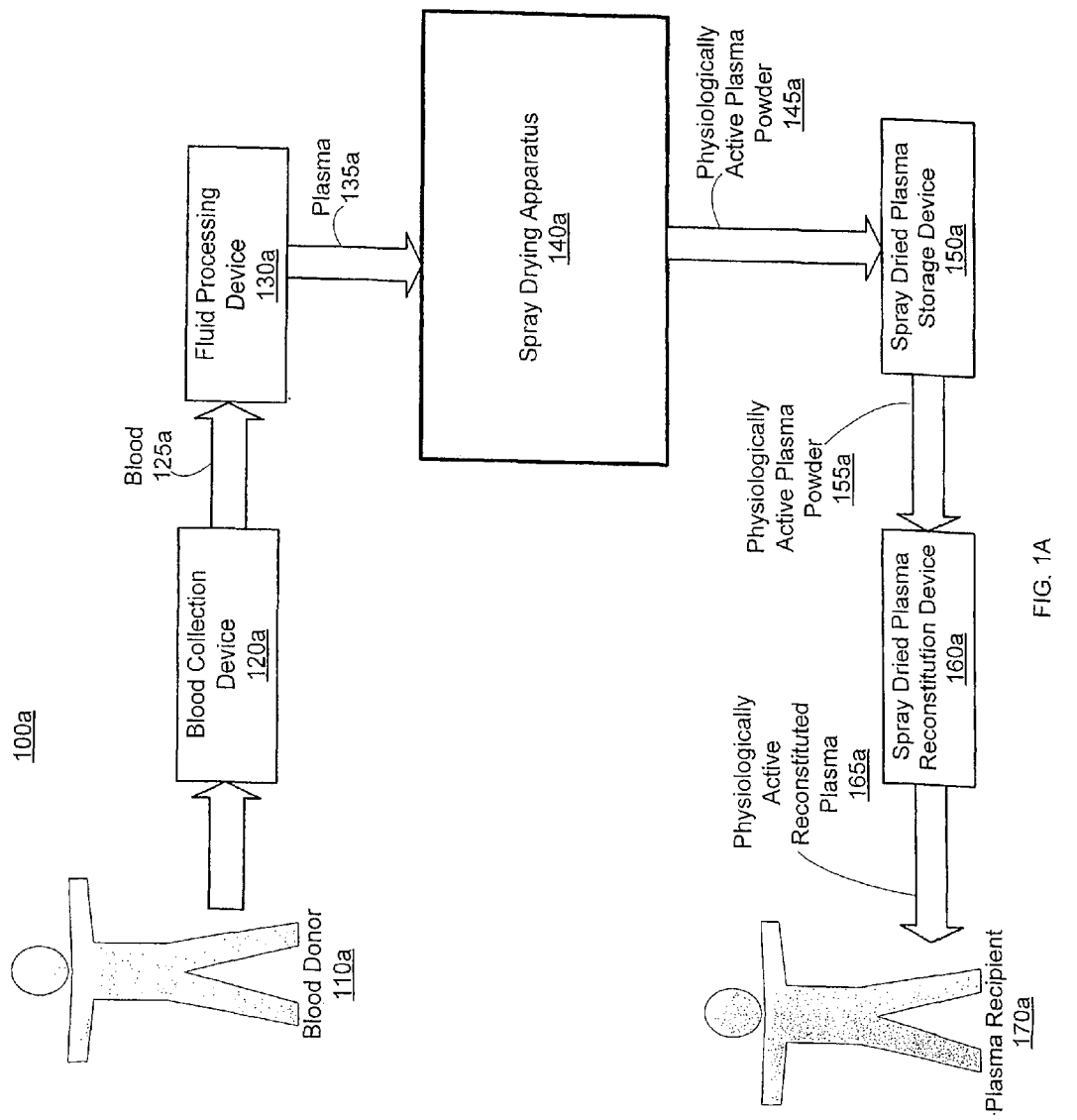

The spray drying system can be utilized to produce physiologically active plasma powder from human plasma. The spray drying system can dry the human plasma to form the physiologically active plasma powder while not overheating the human plasma which causes proteins within the human plasma to lose their efficacy (i.e., denatures the proteins). The spray drying system can utilize a heating source to heat the human plasma via a heated air stream. The heating of the human plasma via the heated air stream can remove the moisture from the human plasma while not denaturing the proteins within the human plasma thereby increasing the efficacy of the physiologically active plasma powder. For example, in some embodiments the moisture is removed by evaporative processes only, and not boiling.

The spray drying system can dry human plasma in a sterile, isolated environment. That is, during the spray drying process, the human plasma and resulting dried plasma powder can be kept isolated from any non sterile contaminates. Accordingly, the dried plasma powder product can be stored for time periods of months or more without the possibility of the growth of, e.g., bacterial contaminates.

As used herein, the term physiologically active plasma powder refers to any plasma powder which, when reconstituted, includes proteins that have not been damaged to such an extent to lose substantially all of their physiological efficacy. The physiological activity of a plasma powder, in its reconstituted form, may by indicated by a number of parameters known in the art including, but not limited to: Prothrombin Time (PT), Activated Partial Thromboplastin Time (aPTT), Fibrinogen level, Protein C level, and Protein S level. The physiological activity of a plasma powder, in its reconstituted form, may be indicated by coagulation factor levels known in the art including, but not limited to: Factor II, Factor V, Factor VII, Factor VIII, Factor IX, and Factor X. These parameters may be measured using techniques known in the art, e.g., using instruments available from DIAGNOSTICA STAGO, Inc. of Five Century Drive Parsippany, N.J., 07054.

Devices and techniques described herein may be used to produce plasma powder which, when reconstituted, has substantially the same level of physiological activity as, e.g., native plasma, fresh frozen plasma (FFP), or plasma frozen within 24 hours of phlebotomy (FP24), Thawed Plasma, or Liquid Plasma.

For example, as set forth in the Circular of Information For The Use of Human Blood Components (August 2009, available online at http://www.aabb.org/resources/bct/Documents/coi0809r.pdf) prepared jointly by the Advancing Transfusion and Cellular Therapies Worldwide (AABB), the American Red Cross, America's Blood Centers, and the Armed Services Blood Program (ASBP), FFP is prepared from a whole blood or apheresis collection and frozen at −18° C. or colder within the time frame as specified in the directions for use for the relevant blood collection, processing, and storage system (e.g., frozen within eight hours of draw). On average, units contain 200 to 250 mL, but apheresis derived units may contain as much as 400 to 600 mL. FFP contains plasma proteins including all coagulation factors. FFP contains high levels of the labile coagulation Factors V and VIII. FFP should be infused immediately after thawing or stored at 1 to 6° C. for up to 24 hours. If stored longer than 24 hours, the component must be relabeled or discarded depending on the method of collection. FFP serves as a source of plasma proteins for patients who are deficient in or have defective plasma proteins.

FP24 is prepared from a whole blood collection and must be separated and placed at −18° C. or below within 24 hours from whole blood collection. The anticoagulant solution used and the component volume are indicated on the label. On average, units contain 200 to 250 mL. This plasma component is a source of non labile plasma proteins. Levels of Factor VIII are significantly reduced and levels of Factor V and other labile plasma proteins are variable compared with FFP. FP24 should be infused immediately after thawing or stored at 1 to 6° C. for up to 24 hours. If stored longer than 24 hours, the component must be relabeled or discarded. This plasma component serves as a source of plasma proteins for patients who are deficient in or have defective plasma proteins. Coagulation factor levels might be lower than those of FFP, especially labile coagulation Factors V and VIII.

Thawed Plasma is derived from FFP or FP24, prepared using aseptic techniques (closed system), thawed at 30 to 37° C., and maintained at 1 to 6° C. for up to 4 days after the initial 24-hour post-thaw period has elapsed. Thawed plasma contains stable coagulation factors such as Factor II and fibrinogen in concentrations similar to those of FFP, but variably reduced amounts of other factors (e.g., as show in FIG. 15).

Liquid Plasma is separated no later than 5 days after the expiration date of the Whole Blood and is stored at 1 to 6° C. The profile of plasma proteins in Liquid Plasma is poorly characterized. Levels and activation state of coagulation proteins in Liquid Plasma are dependent upon and change with time in contact with cells, as well as the conditions and duration of storage. This component serves as a source of plasma proteins. Levels and activation state of coagulation proteins are variable and change over time.

FFP and FP24 are indicated in the following conditions: management of preoperative or bleeding patients who require replacement of multiple plasma coagulation factors (e.g., liver disease, DIC); patients undergoing massive transfusion who have clinically significant coagulation deficiencies; patients taking warfarin who are bleeding or need to undergo an invasive procedure before vitamin K could reverse the warfarin effect or who need only transient reversal of warfarin effect; for transfusion or plasma exchange in patients with thrombotic thrombocytopenic purpura (TTP); management of patients with selected coagulation factor deficiencies, congenital or acquired, for which no specific coagulation concentrates are available; management of patients with rare specific plasma protein deficiencies, such as C1 inhibitor, when recombinant products are unavailable.

Thawed Plasma is indicated for: management of preoperative or bleeding patients who require replacement of multiple plasma coagulation factors except for patients with a consumptive coagulopathy; initial treatment of patients undergoing massive transfusion who have clinically significant coagulation deficiencies; and patients taking warfarin who are bleeding or need to undergo an invasive procedure before vitamin K could reverse the warfarin effect or who need only transient reversal of warfarin effect. Thawed Plasma should not be used to treat isolated coagulation factor deficiencies where other products are available with higher concentrations of the specific factor(s).

Liquid Plasma is indicated for initial treatment of patients who are undergoing massive transfusion because of life-threatening trauma/hemorrhages and who have clinically significant coagulation deficiencies.

Various embodiments of plasma powder of the type described herein, may exhibit levels of physiological activity equivalent or superior to FFP or FP24, and thus may be suitable, e.g., for the uses of Liquid Plasma, Thawed Plasma, FP24, and FFP, as described above. For example, FIG. 15 shows the coagulation factor activity for thawed plasma derived from FFP for several coagulation factors. Plasma powder of the type described herein may exhibit substantially similar coagulation activity for one or more or all of the listed factors.

Various embodiments of plasma powder of the type described herein, may exhibit a PT (in seconds) of 48 or less, 31 or less, 15 or less, etc. For example, the plasma powder may have a PT (in seconds) in the range of 10-48, in the range of 14-31, in the range of 10-15, etc.

Various embodiments of plasma powder of the type described herein, when reconstituted, may exhibit an aPTT (in seconds) of 95 or less, 66 or less, 35 or less, etc. For example, the plasma powder may have an aPTT (in seconds) in the range of 30-95, in the range of 28-66, in the range of 30-35, etc.

Various embodiments of plasma powder of the type described herein, when reconstituted, may exhibit a Fibrinogen level (in mg/dL) of 100 or more, 110 or more, 223 or more, etc. For example, the plasma powder may have a Fibrinogen level (in mg/dL) in the range of 100-500, in the range of 110-300, in the range of 223-500, etc.

Various embodiments of plasma powder of the type described herein, when reconstituted, may exhibit a Protein C level (in IU/dL) of 54 or more, 55 or more, 74 or more, etc. For example, the plasma powder may have a Protein C level (in IU/dL) in the range of 54-154, in the range of 55-130, in the range of 74-154, etc.

Various embodiments of plasma powder of the type described herein, when reconstituted, may exhibit a Protein S level (in IU/dL) of 56 or more, 55 or more, 61 or more, etc. For example, the plasma powder may have a Protein S level (in IU/dL) in the range of 56-138, in the range of 55-110, in the range of 61-138, etc.

Various embodiments of plasma powder of the type described herein, when reconstituted, may exhibit a Factor V level (in IU/dL) of 17 or more, 30 or more, 54 or more, etc. For example, the plasma powder may have a Factor V level (in IU/dL) in the range of 17-135, in the range of 30-110, in the range of 63-135, etc.

Various embodiments of plasma powder of the type described herein, when reconstituted, may exhibit a Factor VII level (in IU/dL) of 31 or more, 30 or more, 54 or more, etc. For example, the plasma powder may have a Factor VII (in IU/dL) level in the range of 31-172, in the range of 30-110, in the range of 54-172, etc.

Various embodiments of plasma powder of the type described herein, when reconstituted, may exhibit a Factor VIII level (in IU/dL) of 10 or more, 25 or more, 47 or more, etc. For example, the plasma powder may have a Factor VIII (in IU/dL) level in the range of 10-195, in the range of 25-90, in the range of 47-195, etc.

Various embodiments of plasma powder of the type described herein, when reconstituted, may exhibit a Factor IX level (in IU/dL) of 13 or more, 25 or more, 70 or more, etc. For example, the plasma powder may have a Factor IX level (in IU/dL) in the range of 13-141, in the range of 25-135, in the range of 70-141, etc.

Various embodiments of the plasma powder may exhibit any combination of the above activity levels.

Some embodiments of plasma powder of the type described herein may be a dry powder containing, e.g., less than 1% moisture by weight, less than 5% moisture by weight, less than 10% moisture by weight, etc. Some embodiments may have powder with moisture content in the range, e.g., of 3-5% moisture by weight.

Various embodiments of plasma powder of the type described herein, may be a fine powder having an average particle size less than 100 microns, less than 50 microns, less than 30 microns, less than 10 microns, less than 5 microns, less than 1 micron, etc. For example, the powder may have an average particle size in the range of 1-30 microns. In some embodiments, the powder has a maximum particle size of less than 100 microns, less than 50 microns, less than 30 microns, less than 10 microns, less than 5 microns, less than 1 micron, etc. For example, the powder may have a maximum particle size in the range of 1-30 microns. Such fine powders may advantageously be reconstituted quickly and efficiency, e.g., using the reconstitution techniques described herein.

Various embodiments of plasma powder of the type described herein may be composed of 10% or more, 20% or more, 30% or more, 40% or more, 50% or more dried proteins by weight. In some embodiments, when reconstituted at a ratio of 0.09 grams of powder to 1 mL of reconstituting fluid, the reconstituted plasma has a protein concentration ration of about 48 mg/mL, e.g., in the range of 45-55 mg/mL.

Advantageously, embodiments of the dried plasma powders described herein may be stored for extended storage times while maintaining a high level of physiological activity. Various embodiments of plasma powder of the type described herein may be stored in a closed sterile container (e.g., a sealed sterile bag) for a storage time, and then, upon reconstitution, exhibit any of the levels of physiological activity set forth above. For example, in various embodiments, the stored powder storage time may be up to 1 day, 1 week, 1 month, 2 months, 3 months, 4 months, 5 months, 6 months, 7 months, 8 months, 9 months, 1 year, 2 years, 5 years, or even longer. After the storage time, the powdered may be reconstituted to form a reconstituted plasma having level of physiological activity equal to or greater than, e.g., Liquid Plasma, Thawed Plasma, FP24, or FFP. Various embodiments of the dried plasma, during storage experience a rate of degradation (i.e., loss of physiological activity) comparable or less than that of e.g., Liquid Plasma, Thawed Plasma, FP24, or FFP.

FIG. 1A is a diagram of an exemplary spray drying system 100a for producing plasma powders of the type described above. The system 100a includes a spray drying apparatus 140a. A blood donor 110a donates blood 125a via a blood collection device 120a. The blood collection device 120a (e.g., needle and bag, etc.) collects blood 125a from a blood donor 110a (e.g., human). A fluid processing device 130a processes the blood 125a to separate plasma 135a from the blood 125a (e.g., a centrifuge device, a reactant, etc.).

The plasma 135a is transferred to the spray drying apparatus 140a (e.g., a pump, gravity, etc.). The spray drying apparatus 140a produces physiologically active plasma powder 145a via the spray drying techniques described herein. The physiologically active plasma powder 145a is stored in a spray dried plasma storage device 150a (e.g., a plastic bag, a glass container, a sealed bag, a sealed container, etc.).

A spray dried plasma reconstitution device 160a reconstitutes the physiologically active plasma powder 155a with a reconstitution fluid (e.g., water, glycine, saline solution, a buffer solution, a blood substitute, etc.) to form physiologically active reconstituted plasma 165a. In some embodiments, two reconstitution fluids can be used; e.g., in one embodiment, a mixture of distilled Water and 1.5% (200 mM glycine) (available from Baxter International Inc. of Deerfield, Ill.) is used.

The plasma powder 145a may exhibit, a recovery rate for the protein between the plasma and the physiologically active reconstituted plasma, of at least 50%, at least 60%, at least 70%, at least 80%, at least 90%, etc. In some embodiments, the reconstituted plasma has protein levels comparable to or better than FFP or FP24. The physiologically active reconstituted plasma 165a is administered to a plasma recipient 170a (e.g., via an intravenous injection, applied to a wound on the plasma recipient, etc.).

In other embodiments, the blood collection device 120a and the fluid processing device 130a are an integrated device that collects the blood, separates the plasma from the blood, and returns the remaining parts of the blood back to the blood donor 110a. This process can be referred to as apheresis and can, for example, utilize an apheresis device.

Figure 1B:
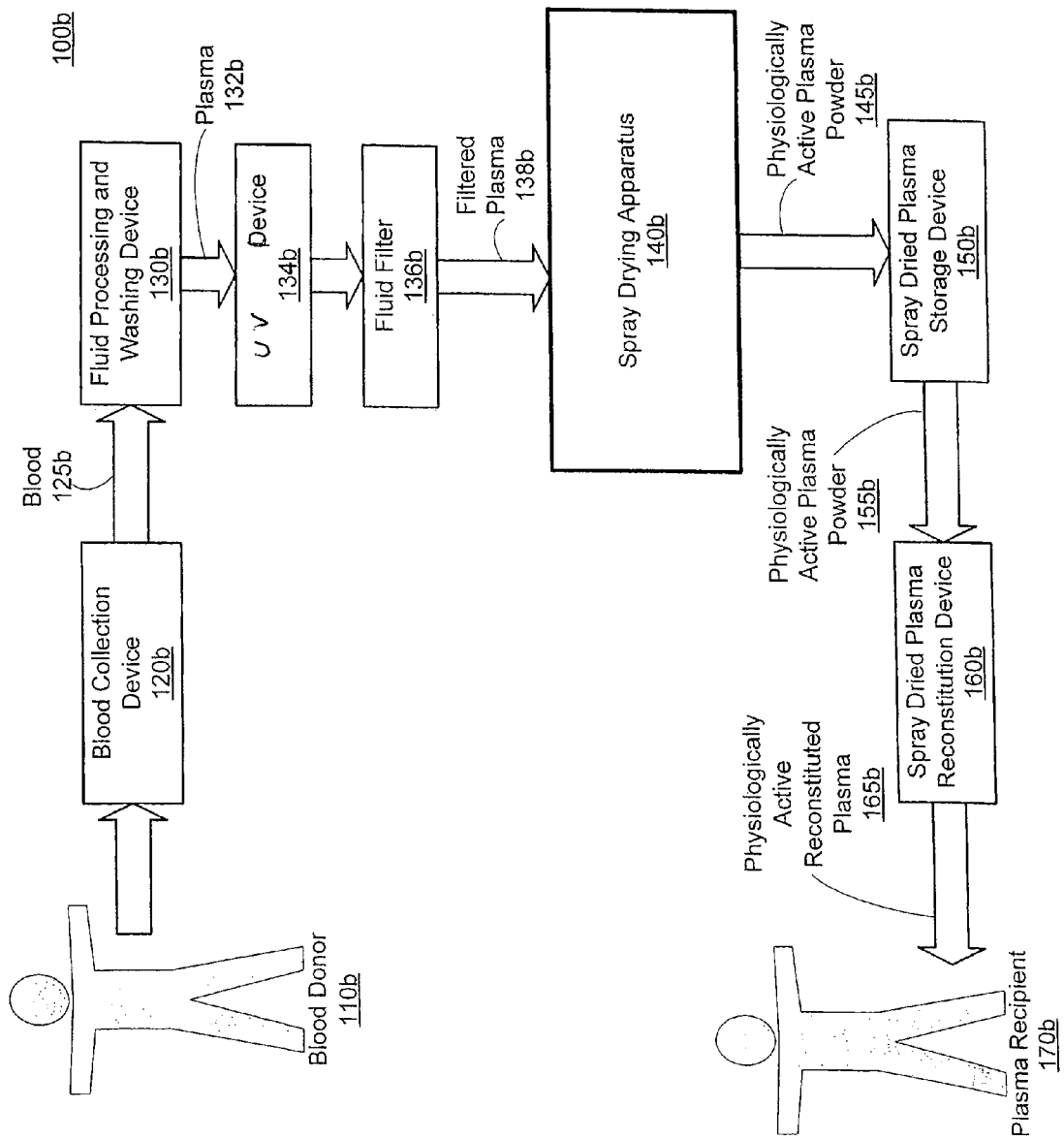

FIG. 1B is a diagram of an exemplary spray drying system 100b. The system 100b includes a spray drying apparatus 140b. A blood collection device 120b (e.g., needle and bag, etc.) collects blood 125b from a blood donor 110b (e.g., human).

A fluid processing and washing device 130b processes the blood 125b to separate plasma 132b from the blood 125b (e.g., a centrifuge device, a reactant, etc.). The fluid processing and washing device 130b washes the plasma 132b to remove one or more antigens (e.g., virus, allergen, etc.). The washing of the plasma 132b by the fluid processing and washing device 130b can reduce the antigens on the plasma 132b by a factor of at least 100, or at least $10^3$, or at least $10^4$, or at least $10^5$.

The fluid processing and washing device 130b transfers the plasma 135a through a ultraviolet device 134b and a fluid filter 136b (e.g., a pump, gravity, etc.). The ultraviolet device 134b irradiates the plasma 132b with ultraviolet radiation to destroy one or more antigens (e.g., virus, allergen, etc.). The irradiation of the plasma 132b by the ultraviolet radiation can reduce the antigens on the plasma 132b by a factor of at least 100, or at least $10^3$, or at least $10^4$, or at least $10^5$. The fluid filter 136b filters one or more antigens from the plasma 132b (e.g., biofilter, activated charcoal filter, etc.). The filtering of the plasma 132b by the fluid filter 132b can reduce the antigens on the plasma 132b, e.g., by a factor of at least 100, or at least $10^3$, or at least $10^4$, or at least $10^5$. An advantage of washing, irradiating, and/or filtering the plasma 132b is that this process cleans the plasma 132b so that a plurality of units of plasma can pooled together for processing by the spray drying apparatus 140b, thereby increasing the efficiency of the spray drying processing by allowing more plasma to be spray dried during a drying cycle. After the plasma 132b is processed by the ultraviolet device 134b and the fluid filter 136b, filtered plasma 138b is transferred to the spray drying apparatus 140b.

The spray drying apparatus 140b produces physiologically active plasma powder 145b via the spray drying techniques described herein. The physiologically active plasma powder 145b is stored in a spray dried plasma storage device 150b (e.g., a plastic bag, a glass container, a sealed bag, a sealed container, etc.).

A spray dried plasma reconstitution device 160b reconstitutes the physiologically active plasma powder 155b with a reconstitution fluid (e.g., water, glycine, any suitable irrigation fluid, a blood substitute, etc.) to form physiologically active reconstituted plasma 165b. The physiologically active reconstituted plasma 165b is administered to a plasma recipient 170b (e.g., via an intravenous injection, applied to a wound on the plasma recipient, etc.).

In some embodiments, the reconstitution fluid includes glycine. Not wishing to be bound by theory, in some embodiments, it is believed that the glycine can enable the physiologically active reconstituted plasma 165b to act as a volume expander and can increase the efficacy of the plasma. In some embodiments, the glycine may advantageously affect the pH level of the reconstituted plasma, thereby increasing the efficacy of the plasma. In one embodiment, the reconstitution fluid includes 1.5% glycine. In other embodiments, reconstitution fluid includes glycine concentrations of 0.1%, 0.5%, 1.0%, 1.25%, 1.3%, 1.4%, 1.6%, 1.7%, 1.75%, 2%, 2.5%, 3%, 4%, or 5%. As discussed in greater detail below, in some embodiments, plasma powder reconstituted with glycine exhibits improved PT, aPTT, and coagulation factor levels in comparison to plasma powder reconstituted with water.

In various embodiments, other reconstitution fluids may be used including, e.g., solutions including a buffering agent (e.g., a phosphate buffer, HCl, buffer Citric Acid buffer, etc.). As with glycine, these reconstitution fluids may be used to adjust the pH level of the reconstituted plasma to a desired value or range. For example, in some embodiments, the spray dried plasma may have a pH level which differs from native plasma, and a buffering agent may be used to adjust the pH level of the reconstituted plasma to more closely match that of the native plasma.

Figure 2:
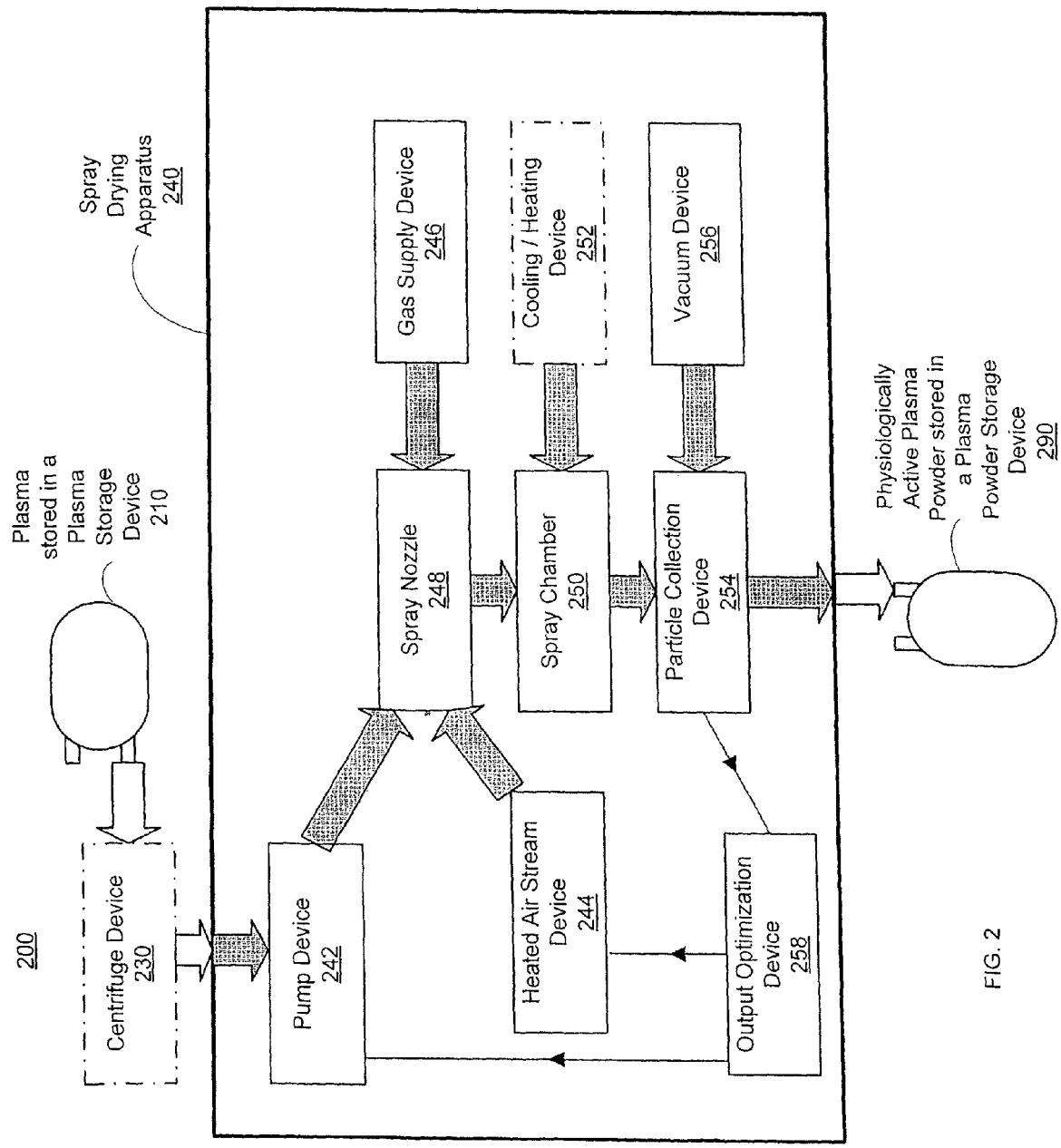

FIG. 2 is a diagram of another exemplary spray drying system 200. The system 200 receives plasma stored in a plasma storage device 210 and includes a centrifuge device 230, a spray drying apparatus 240. The system 200 stores plasma powder in a plasma powder storage device 290. The spray drying apparatus 240 includes a pump device 242, a heated air stream device 244, a gas supply device 246, a spray nozzle 248, a spray chamber 250, a cooling/heating device 252, a particle collection device 254, a vacuum device 256, and an output optimization device 258.

The centrifuge device 230 centrifuges the plasma stored in a plasma storage device 210 to maximize the delivery of particular particles of the plasma to the spray drying apparatus 240 (e.g., platelets, protein, type of plasma, etc.). The centrifuge device 230 moves the centrifuged plasma to the spray drying apparatus 240 (e.g., directly via a pump, indirectly via gravity, etc.). Although FIG. 2 illustrates the system 200 including the centrifuge device 230, in some embodiments of the system 200, the centrifuge device 230 is not included in the system 200. For example plasma obtained from any suitable source/supplier can be input into the spray drying system.

The pump device 242 pumps the plasma to the spray nozzle 248 at a set pump setting (e.g., corresponding to a flow rate of about 11.5 mL/min, in the range of 9 to 15 mL/min, etc.). In some embodiments, the plasma can be combined with the reagent or any other type of substance (e.g., blood thinner, water, glycine, blood substitute, etc.) prior to exiting the nozzle 248. In other embodiments, the plasma is not combined with any substance.

The heated air stream device 244 provides a heated, dehumidified air stream to the spray nozzle 248 (e.g., 107° C. at 5% humidity, 109° C. at 25% humidity, etc.). Some embodiments, e.g., as described below, may include a separate heater and dehumidifier for providing the heated dehumidified stream of air.

The gas supply device 246 provides a non reactive gas (e.g., nitrogen, air, carbon dioxide, helium, etc.) at a spray flow rate (e.g., continuous, intermittent, etc.) to the spray nozzle 248. As used herein, a non reactive gas is one which does not chemically react with the plasma or heated air stream during the operation of the spray drying system. The non reactive gas may be, e.g., an inert gas, or a non inert gas which does not react under the operating conditions of the system. In one embodiment, the spray nozzle 248 combines the non reactive gas and the plasma to atomize the plasma into the spray chamber 250. The spray cone of atomized plasma exiting the nozzle 248 is treated by the heated air stream, to dry the atomized particles.

The cooling/heating device 252 or separate heating or cooling devices can heat and/or cool parts of the spray chamber 250 (e.g., to remove remaining moisture, to stop the denaturing of the proteins in the plasma, etc.). The particle collection device 254 collects the spray dried plasma utilizing the vacuum device 256 (e.g., via a cyclone affect). For example, the vacuum device 256 creates a vacuum that pulls the atomized particles into the particle collection device 254 (e.g., particle filter, cyclone trap, etc.). The physiologically active plasma powder is stored in a plasma powder storage device 290. Additionally or alternatively, a pump or other similar devices may be used to provide air flow to move the particles through the collection device 254.

The output optimization device 258 measures the output temperature of the atomized particles after they have been emitted from the spray nozzle 248, e.g., as they enter the spray chamber 250, at the interface between the spray chamber 250 and the collection device 254, or at another suitable position. In some embodiments, the temperature of the particles is not measured directly; instead, an indirect indicator (e.g., an outlet gas temperature) is measured. The temperature of the atomized particles is maintained below a threshold temperature to prevent denaturing of the proteins within the plasma. The output temperature is not directly adjustable. The output optimization device 258 can adjust the pump setting of the pump device 242 and/or the input temperature of the heated air stream device 244 to maintain the output temperature in a selected temperature range.

In some embodiments, the pump setting of the pump device 242 is dynamically adjusted based on the input temperature of the plasma at the spray nozzle 248 and/or the output temperature of the spray dried plasma powder at the spray chamber 250 and/or at the particle collection device 254.

Figure 3A:
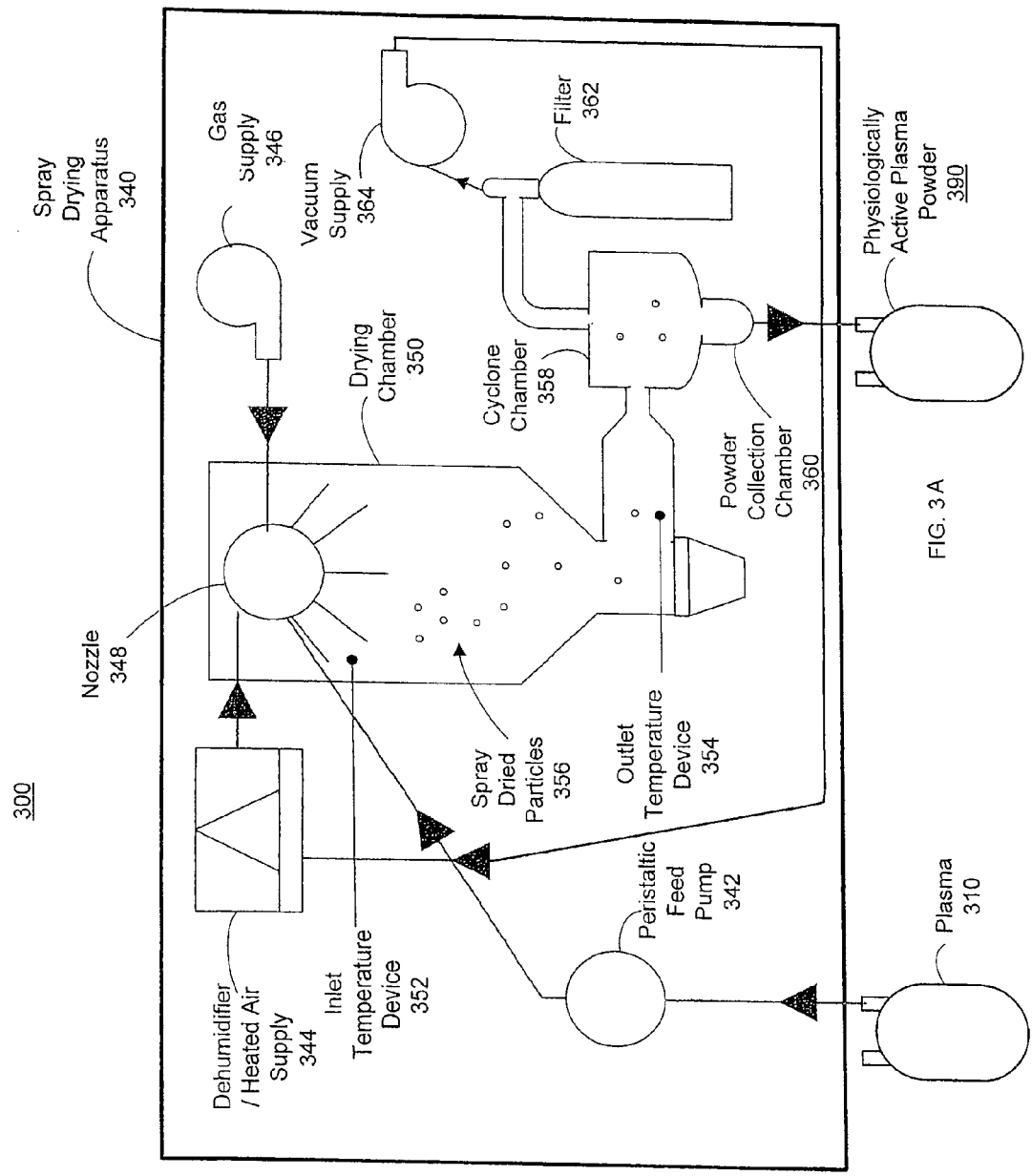

FIG. 3A is a diagram of another exemplary spray drying system 300. The system 300 includes a spray drying apparatus 340. The spray drying apparatus 340 includes a peristaltic feed pump 342, a dehumidifier/heated air supply 344, a non reactive gas supply 346, a nozzle 348, a drying chamber 350, an inlet temperature device 352, an outlet temperature device 354, spray dried particles 356, a cyclone chamber 358, a powder collection chamber 360, a filter 362, and a vacuum supply 364.

The peristaltic feed pump 342 pumps plasma 310 at a pump rate (e.g., continuous, intermittent, etc.) to the nozzle 348. The dehumidifier/heated air supply 344 heats and/or dehumidifies air, output from the vacuum supply 364 and blows a heated, dehumidified air stream at an inlet temperature to the nozzle 348. Preferably the temperature of the air stream is adjustable. The non reactive gas supply 346 supplies a non reactive gas (e.g., nitrogen, helium, carbon dioxide, air, etc.) to the nozzle 348 at a flow rate (e.g., continuous, intermittent, etc.). In one embodiment, the non reactive gas supply 346 is a pressured tank of the non reactive gas with a regulator. In another embodiment, the non reactive gas supply 346 is a pump for pressurizing the non reactive gas. The plasma 310, the heated dehumidified air stream, and the non reactive gas are combined at the nozzle 348 and the atomized plasma is blown into the drying chamber 350.

Figure 3B:
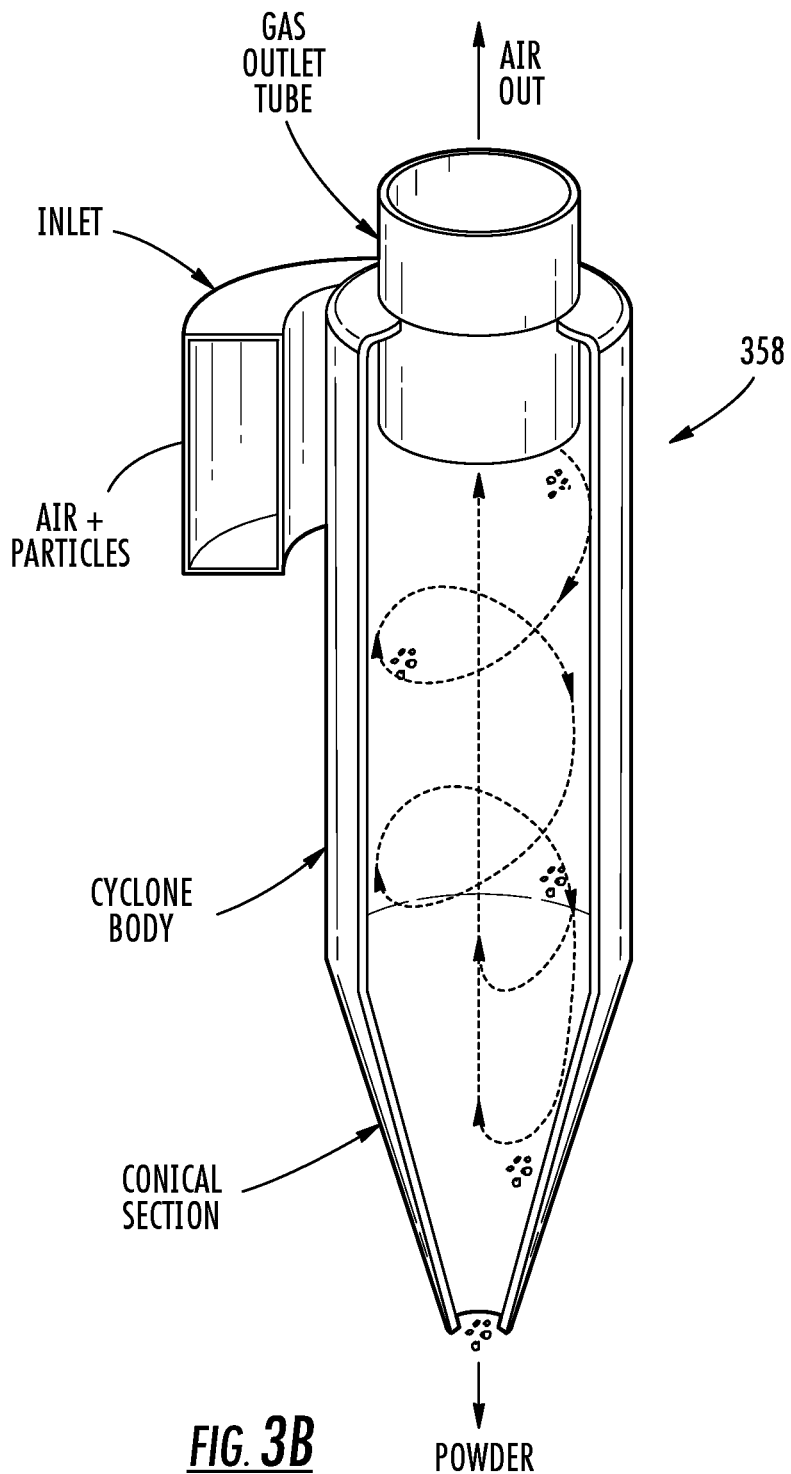

The spray dried particles 356 are moved into the cyclone chamber 358 via the vacuum created by the vacuum supply 364 for cyclonic separation. Cyclonic separation is a method of removing particulates from an air, gas or water stream, without the use of filters, through vortex separation. Rotational effects and gravity are used to separate mixtures of solids and fluids. In some embodiments, the cyclone chamber 358 is a cylindrical body with a tapered conical bottom portion. As shown in FIG. 3B, rotating (air) flow is established within the cyclone chamber 358. Air flows in a spiral pattern, beginning at the top (wide end) of the cyclone chamber and ending at the bottom (narrow) end before exiting the cyclone in a straight stream through the center of the cyclone and out the top. Larger (denser) particles in the rotating stream have too much inertia to follow the tight curve of the stream and strike the outside wall, falling then to the bottom of the cyclone where the particles form a powder that can be collected and removed. In a conical system, as the rotating flow moves towards the narrow end of the cyclone the rotational radius of the stream is reduced, separating smaller and smaller particles. The cyclone geometry, together with flow rate, defines the cut point of the cyclone. This is the size of particle that will be removed from the stream with a 50% efficiency. Particles larger than the cut point will be removed with a greater efficiency, and smaller particles with a lower efficiency. In some embodiments, the surfaces of the cyclone chamber 358 may be treated to avoid adherence of the particles to the walls of the containers, e.g., due to electrostatic effects, by methods and compositions known in the art (e.g., silicone, Teflon, etc.).

Due to the cyclone effect within the cyclone chamber 358, the spray dried particles 356 are collected within the powder collection chamber 360 and other particles are collected by the filter 362 (e.g., a high efficiency particulate air (HEPA) filter, a carbon filter, etc.).

In other embodiments, other particle collection devices may be used including, e.g., an electrostatic particle trap, a gravity based particle trap, a filter, etc.

The physiologically active plasma powder 390 is collected from the powder collection chamber 360 and can be, for example, stored (e.g., via storage container, etc.) and/or used (e.g., applied to a wound of a human, etc.).

In other embodiments, the powder collection chamber 360 is removable from the spray drying apparatus 340.

In some embodiments, the processing of the plasma by the spray drying apparatus 340 is an isolated sterile system. In other words, after the spray drying apparatus 340 starts processing the plasma 310, there is no introduction of any further liquids, solids, and/or gases into the spray drying apparatus 340 that could contaminate the plasma powder. Such a system enables the spray drying apparatus 340 to remain sterile during the processing of the plasma 310.

In some embodiments, the spray drying apparatus 340 operates in a small batch mode. In the small batch mode, the spray drying apparatus 340 can process, e.g., one 400 mL of plasma (e.g., one unit of plasma from a single donor). In this mode of operation, the lines, drying chamber 350, the cyclone chamber 358, and/or the powder collection chamber 360 can be cleaned (e.g., sterilized, dipped in an alcohol bath, wiped by an alcohol wipe, etc.) between processing batches.

In some embodiments, the spray drying apparatus 340 operates in a large batch mode. In the large batch mode, the spray drying apparatus 340 can process, e.g., hundreds of mL of plasma (e.g., multiple units of plasma from a plurality of donors). In this mode of operation, the units of plasma are pooled together for processing. An advantage to the spray drying apparatus 340 is that the units of plasma can be pooled together and then cleaned via the fluid processing and washing device 130b, the ultraviolet device 134b, and/or the fluid filter 135b to provide a safe spray dried plasma powder while reducing the overhead of cleaning the spray drying apparatus 340 between batches. Alternatively, as described in greater detail below, the system may include one or more disposable portions that may be swapped out for new sterile counterparts between batches.

Figure 4A:
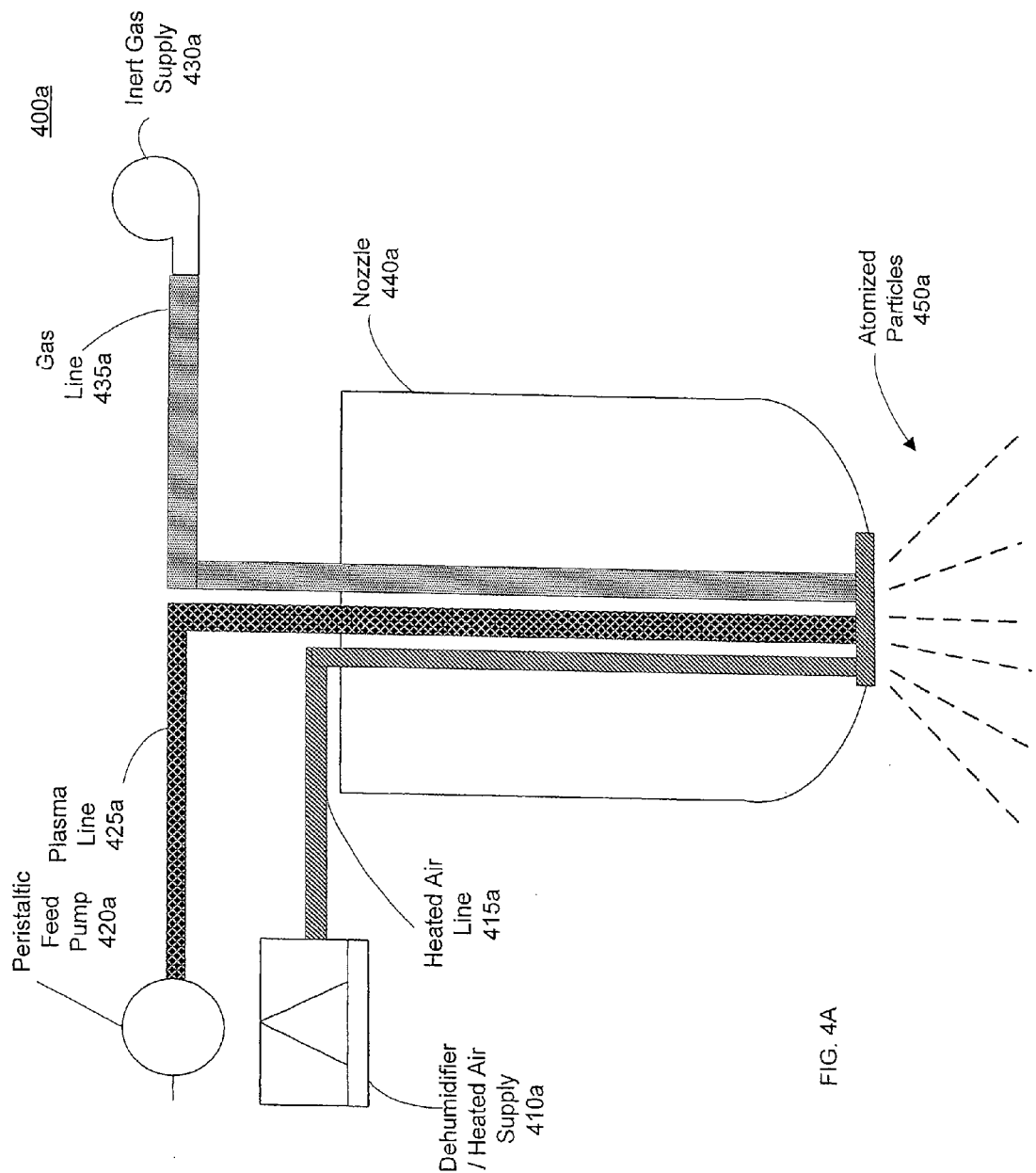

FIG. 4A is a diagram of an exemplary spray nozzle 440a in a spray drying apparatus 400a. The apparatus 400a includes a dehumidifier/heated air supply 410a, a heated air line 415a, a peristaltic feed pump 420a, a plasma line 425a, a non reactive gas supply 430a, and a non reactive gas line 435a. The dehumidifier/heated air supply 410a heats and/or dehumidifies air and pumps the heated air through the heated air line 415a to the nozzle 440a. The peristaltic feed pump 420a pumps plasma through the plasma line 425a to the nozzle 440a. The non reactive gas supply 430a supplies a non reactive gas through the non reactive gas line 435a to nozzle 440a. The non reactive gas, the plasma, and the heated air are combined at the end of the nozzle 440a and the atomized particles 450a exit the nozzle 440a.

In some embodiments, the heated air line 415a may include a sterile filter (e.g., a filter that removes microorganisms, particles, precipitates, and undissolved powders larger than 0.22 micron) located between the air supply 410a and the spray nozzle 440a. Similarly, a sterile filter may be positioned along the non reactive gas line 435a and the spray nozzle 440a. In various embodiments, the nozzle input lines 415a, 425a, and 435a may include detachable connections to the air supply 410a, the pump 420a, the gas supply 430a.

FIG. 4B is a diagram of an exemplary spray nozzle 440b in a spray drying apparatus 400a. A heated air stream 415b from the heated air line 415a and a plasma and non reactive gas mixture 437b from the plasma line 425a and the non reactive gas line 435a is output from the spray nozzle 440b. In this embodiment, the output of the heated air stream 415b is via a circular output port that surrounds the output of the plasma and non reactive gas mixture 437b. Note that, although one configuration is shown, other configurations may be used. For example, in some embodiments, the output port for the plasma and non reactive gas mixture 437b is smaller than the output of the heated air stream 415b.

FIG. 4C is a cross section diagram of the tip 450c of spray nozzle 440b showing the mixture of plasma and non reactive gas to atomize the plasma. The tip includes a first channel 452c that delivers a flow of plasma to the end of the nozzle tip 450c. A second channel 454c is disposed concentrically about the first channel. The second channel 454c delivers non reactive gas to the end of the tip, where it mixes with the flow of plasma. As described above, the atomized plasma may then be mixed with the heated air stream 415b for drying. The mixture of plasma and non reactive gas exits a nozzle output port 456c as an atomized plasma spray. The tip 450c may include a central member 458c located within and extending along the first channel 452c to an end located in or near the nozzle output port 456c. The end of the central member 458c may include a feature 459c which facilitates the atomization of the plasma. The feature 459c (or other portions of the nozzle tip) may be made of a material which resists the build up of residue at the nozzle output port, e.g., ruby.

As illustrated in this example, the plasma and the non reactive gas are mixed together before the air stream mixes into the mixed plasma and the non reactive gas. In some embodiments, the mixture of the non reactive gas and the plasma atomizes the plasma into a spray. In some embodiments, the mixture of the heated air stream into the atomized particles of the plasma removes the moisture and dries the atomized particles to form spray dried plasma particles. Note that although in the example above, the heated air stream is directed in substantially the same direction as the atomized plasma, in some embodiments the heated air stream may be oriented in other directions (e.g., counter to the flow of the atomized plasma). In some embodiments the heated air flow may emanate from a port located at a position in the drying chamber other than on the nozzle.

Figure 5A:
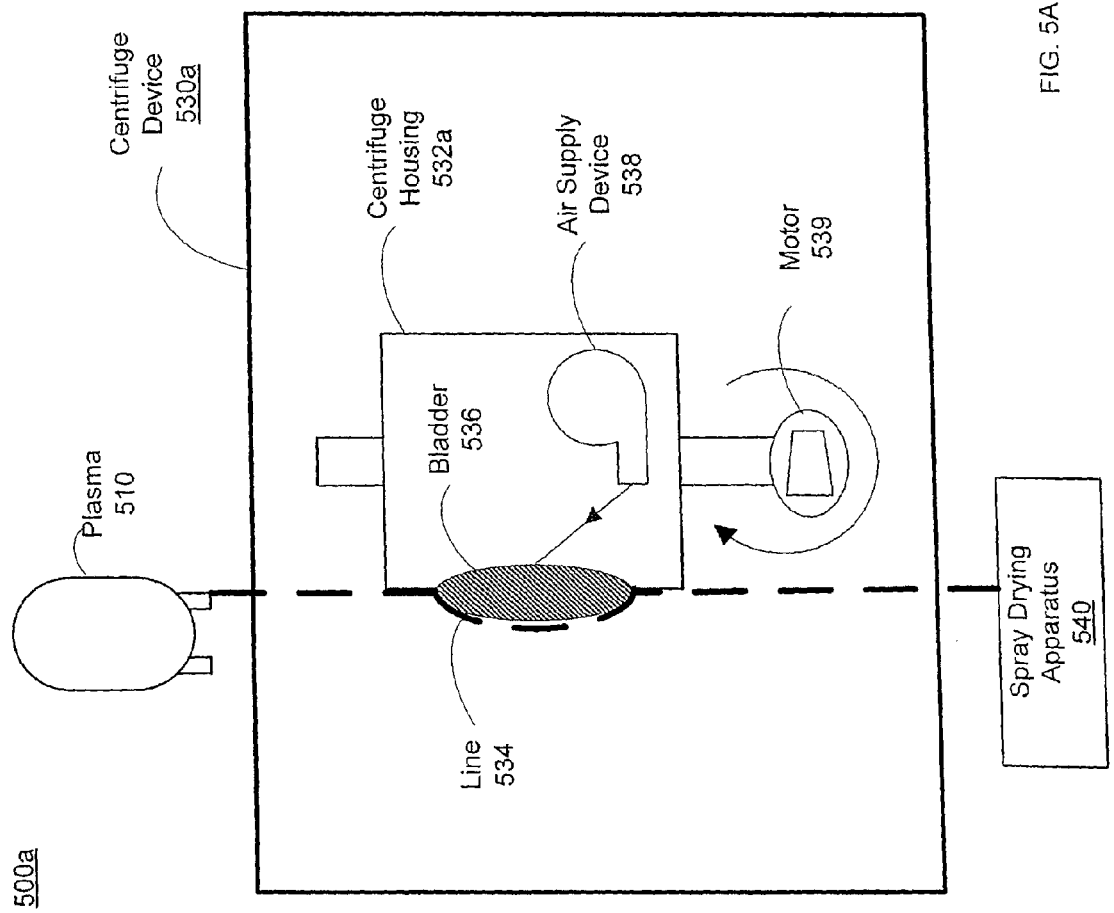

FIG. 5A is a diagram of an exemplary centrifuge system 500a. The system 500a includes plasma 510, a centrifuge device 530a, and a spray drying apparatus 540. The centrifuge device 530a includes a centrifuge housing 532a, a line 534, a bladder 536, an air supply device 538, and a motor 539.

The centrifuge housing 532a rotates, via the motor 539 (e.g., direct drive system, indirect drive system, etc.), to provide inertial forces for the separation of the plasma 510 that is pumped and/or travels (e.g., gravity fed, etc.) through the line 534. The air supply device 538 inflates and/or deflates the bladder 536 to provide for main line geometry as described herein.

Although FIG. 5A depicts the air supply device 538 included in the centrifuge housing 532a, the air supply device 538 can be positioned at any place within or remotely located from the centrifuge housing 532a.

Figure 5B:
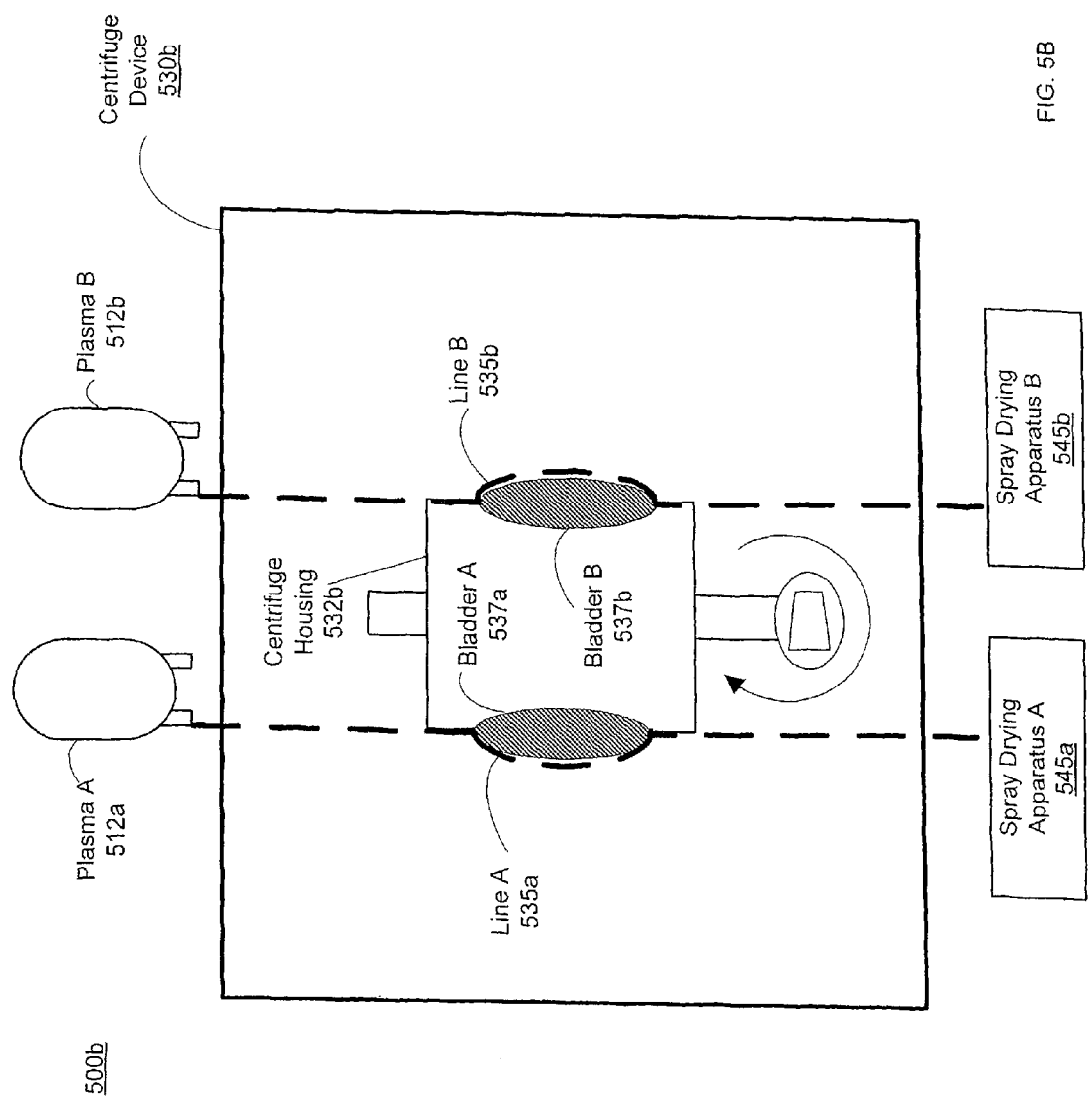

FIG. 5B is a diagram of another exemplary centrifuge system 500b. The system 500b includes plasma A 512a, plasma B 512b, a centrifuge device 530b, a spray drying apparatus A 545a, and a spray drying apparatus B 545b. The centrifuge device 530b includes a centrifuge housing 532b, a line A 535a, a line B 535b, a bladder A 537a, and a bladder B 537b.

The centrifuge housing 532b rotates to provide centrifugal forces for the separation of the plasma A 512a and the plasma B 512b that is pumped and/or travels (e.g., gravity fed, etc.) through the line A 535a and B 535b, respectively. An air supply device (not shown) inflates and/or deflates each bladder A 537a and B 537b to provide for main line geometry for each of the lines A 535a and B 535b, respectively, as described herein.

In other embodiments, a plurality of bladders are located in parallel and in close proximate to the line A 535a. For example, the line A 535a is approximately located to four bladders (i.e., along the main line: Bladder A is positioned at 2 cm, Bladder B is positioned at 4 cm, Bladder C is positioned at 6 cm, and Bladder D is positioned at 8 cm) and each bladder can modify the geometry of the line A 535a approximate to the location of the bladder.

FIG. 6A is a diagram of an exemplary bladder position A 636a for line A 634a in a centrifuge device 530 of FIG. 5. The geometry of the line A 634a functions as a typical centrifugal sedimentation chamber, in which the target biological components are retained in the curve while non target components pass (i.e., Bladder Position 0).

FIG. 6B is a diagram of an exemplary bladder position B 636b for line B 634b in a centrifuge device 530 of FIG. 5. The geometry of the line B 634b functions as a compression chamber, which holds and compresses the target biological component (i.e., Bladder Position +1).

FIG. 6C is a diagram of an exemplary bladder position C 636c for line C 634c in a centrifuge device 530 of FIG. 5. The geometry of the line C 634*c* functions to maximize target component recovery (i.e., Bladder Position 1).

FIG. 7A is a diagram of an exemplary line A 734*a* for a centrifuge device 530 of FIG. 5. The line A 734*a* includes a plurality of fluid lumens 735*a*, 736*a*, and 737*a*.

FIG. 7B is a diagram of an exemplary line B 734*b* for a centrifuge device 530 of FIG. 5. The line B 734*b* includes a plurality of fluid lumens 735*b* and 736*b*.

FIG. 7C is a diagram of an exemplary line C 734*c* for a centrifuge device 530 of FIG. 5. The line C 734*c* includes a plurality of fluid lumens 735*c* and 736*c*.

Figure 13A:
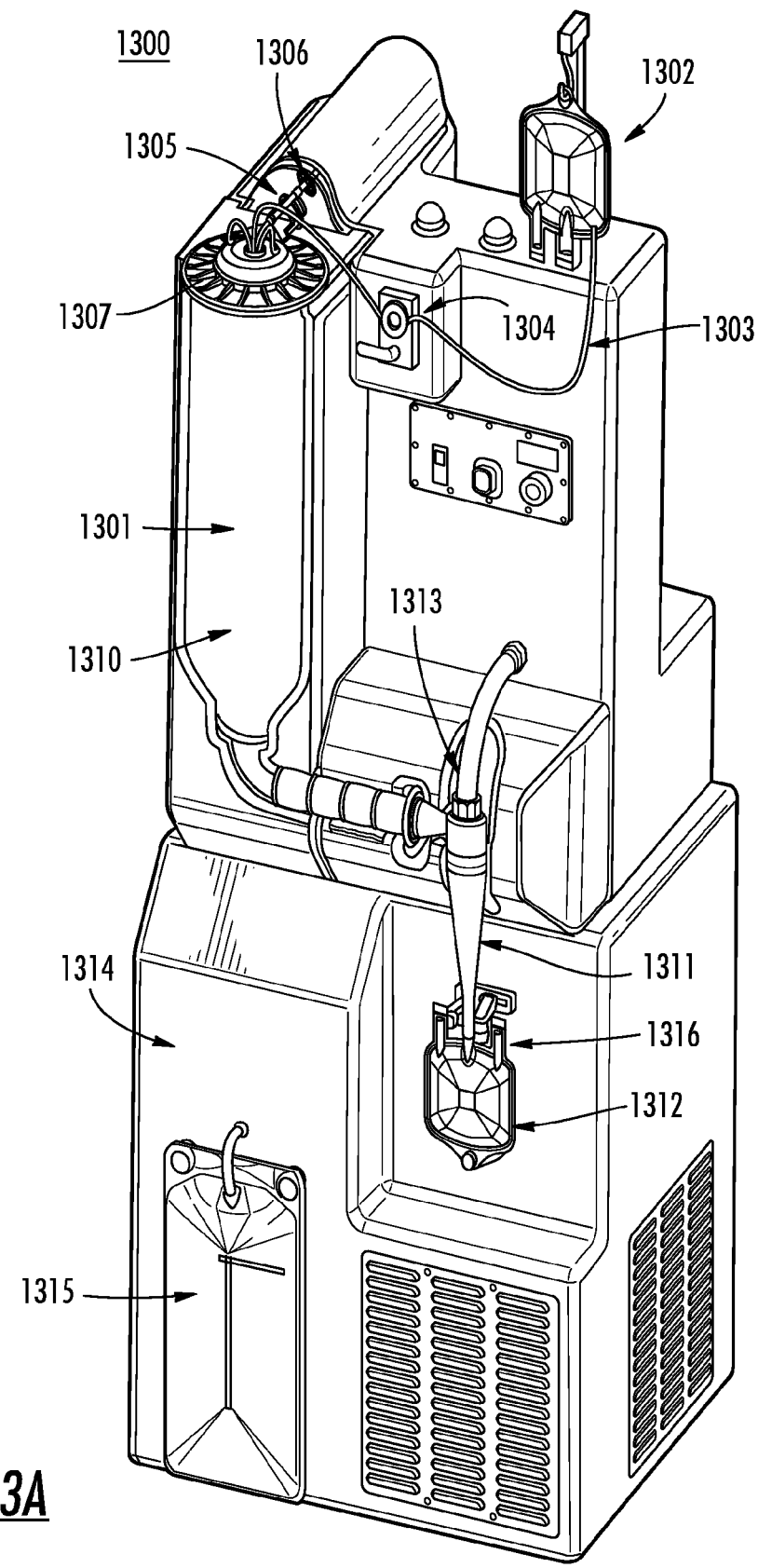
Figure 13B:
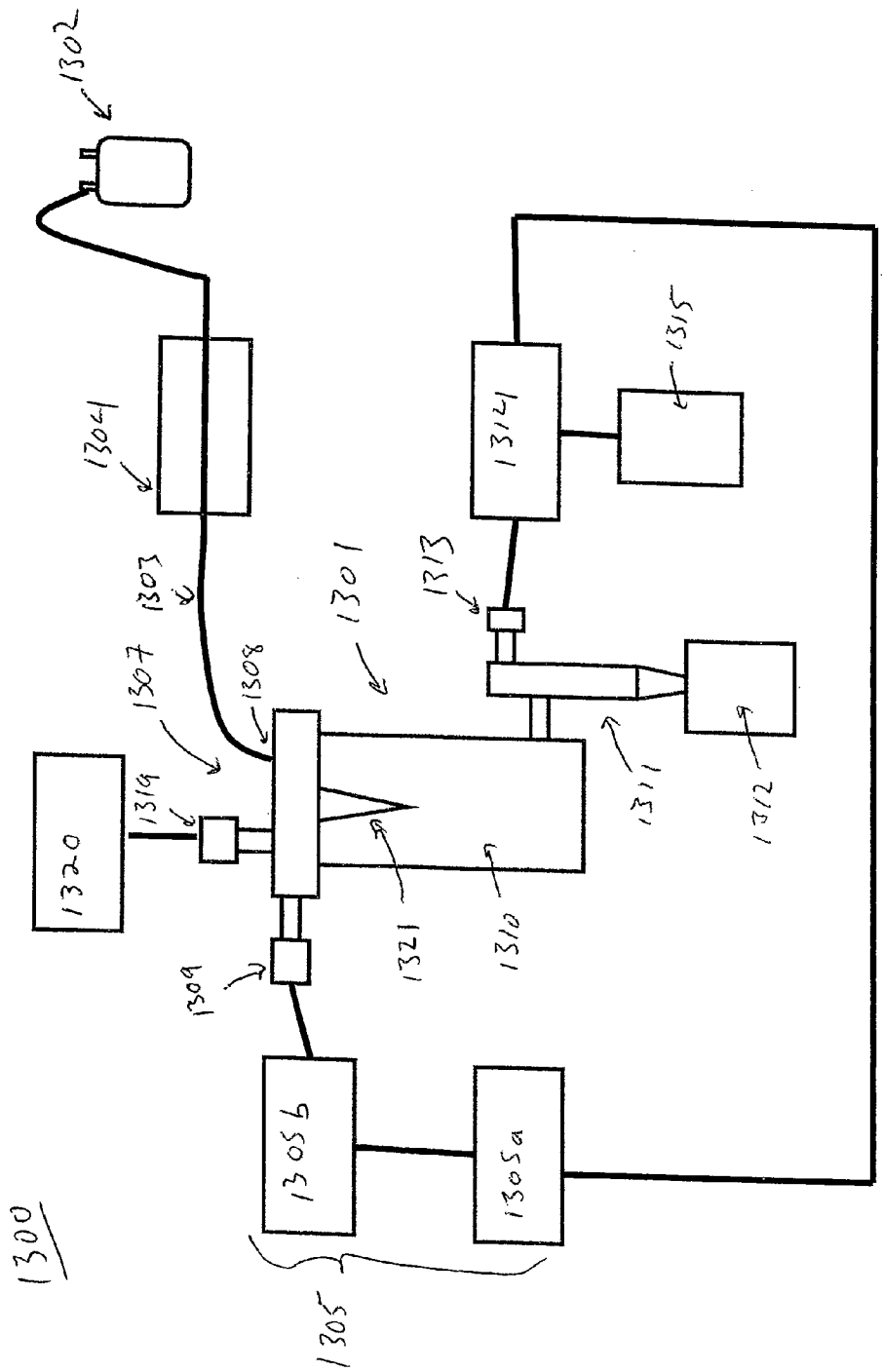
Figure 13D:
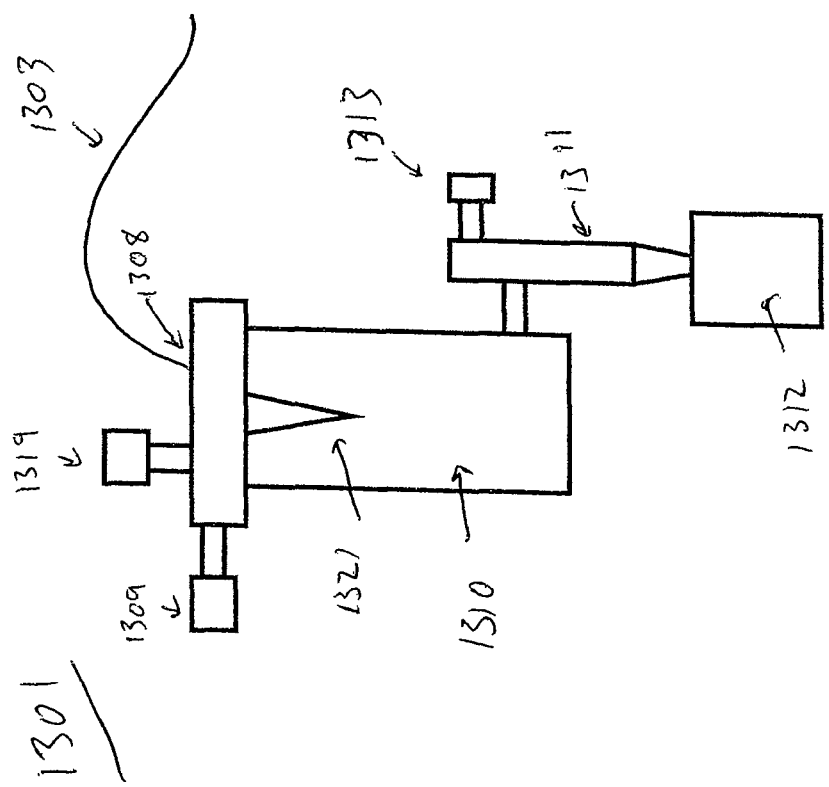

FIG. 13A illustrates a spray drying system 1300, featuring a disposable attachment 1301. FIG. 13B is a schematic of the components of system 1300 with the attachment 1301 attached. FIG. 13C is a schematic of components of system 1300 with the attachment 1301 removed. FIG. 13D is a schematic of the attachment 1301 alone.

The system 1300 includes a plasma source 1302, as shown, a bag of fresh or thawed frozen plasma pumped through a plasma line 1303 by a peristaltic pump 1304. The system further includes a drying gas source 1305 including a pump 1305*a* and a heater 1305*b* for supplying the drying gas (e.g., heated dry air). The system also includes a non reactive spray gas source 1320, e.g., a source of pressurized nitrogen gas.

Figure 13E:
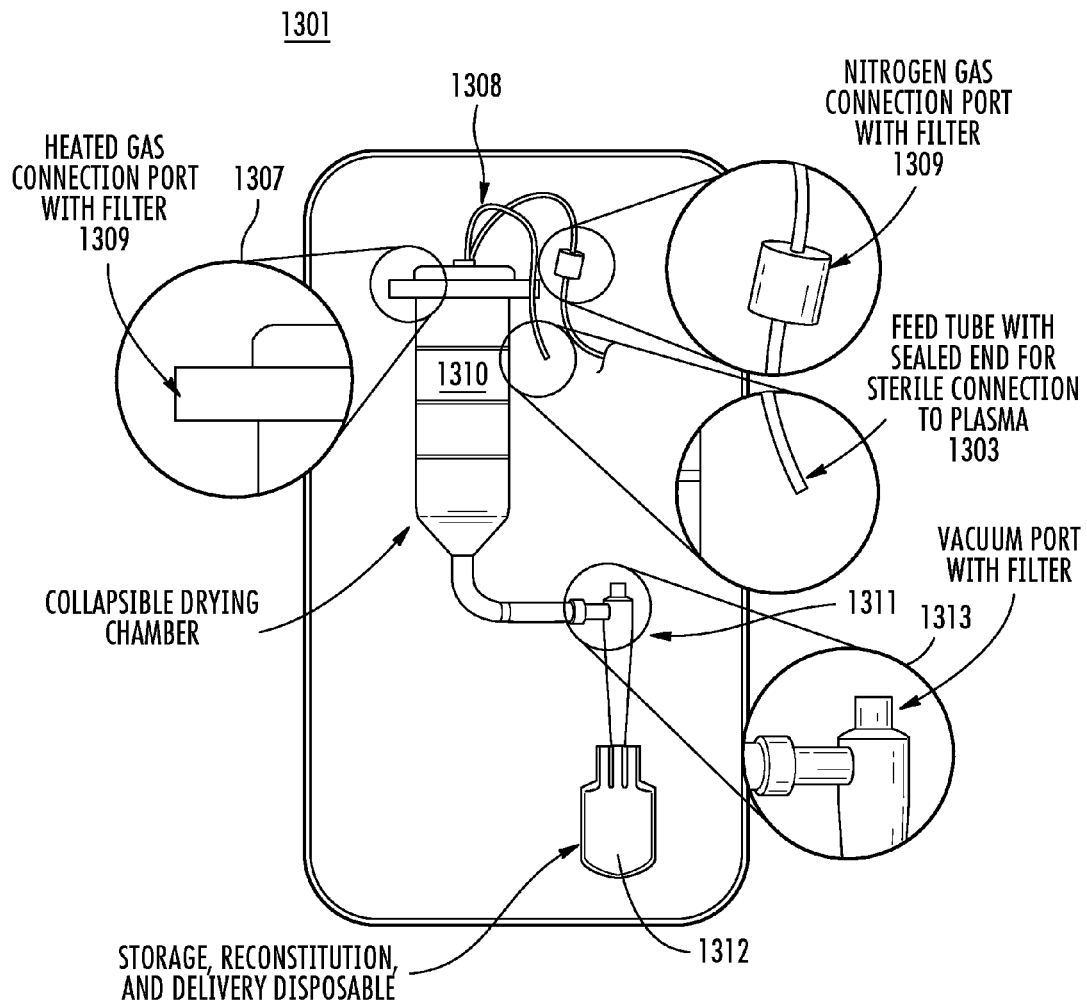
Figure 13F:
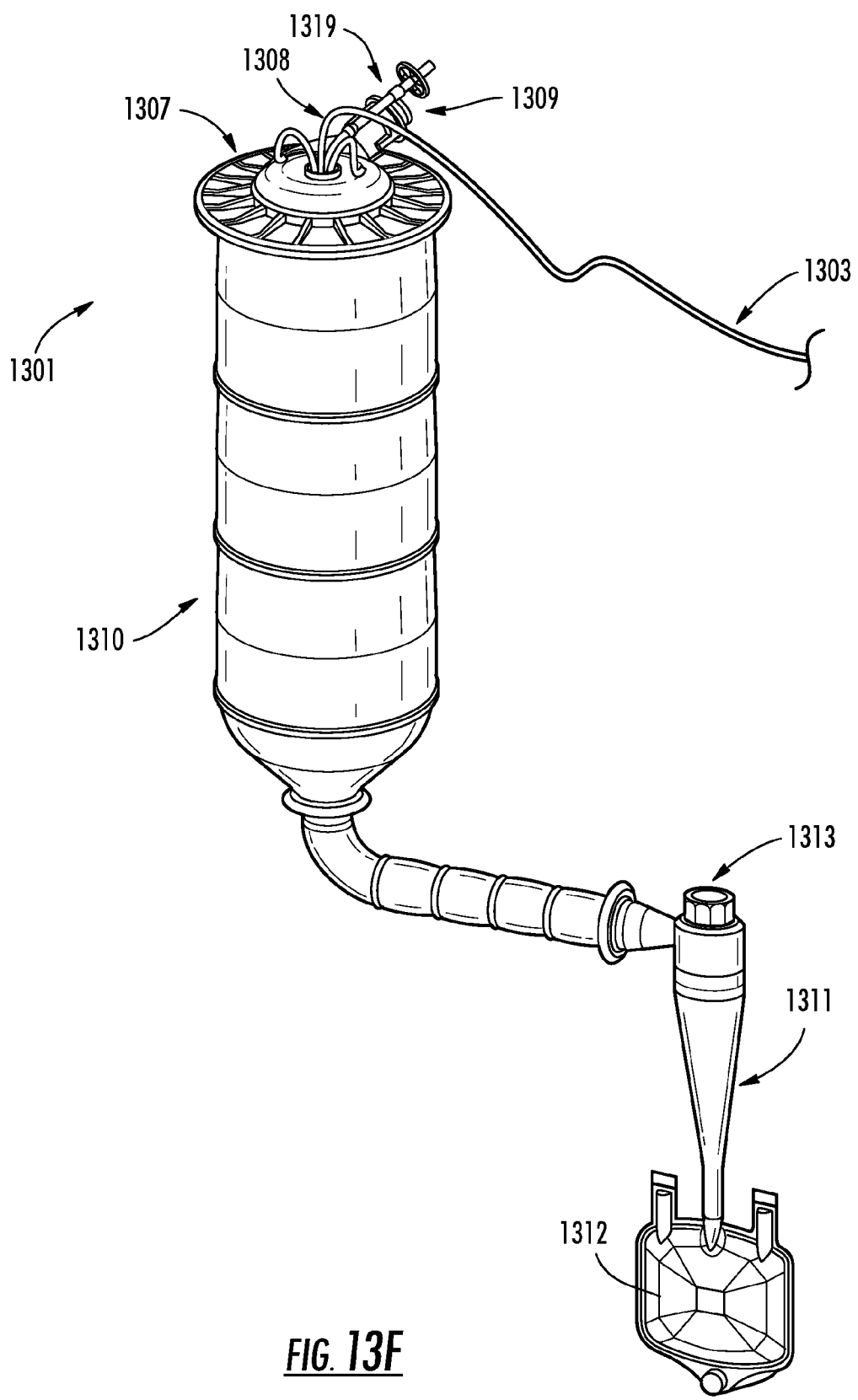

Disposable attachment 1301 (shown in detail in FIGS. 13D-13F) includes spray nozzle assembly 1307 having a spray nozzle 1321 and a plasma input 1308 for sterile coupling to the plasma source 1302. For example, as shown, the plasma input includes a feed tube 1303 with a sealed end for sterile connection to the plasma unit. In other embodiments, other types of sterile connectors or docks may be used.

The nozzle assembly 1307 also includes a drying gas input 1309 for connection to the drying gas source 1305. The drying gas connection is a sterile connection, e.g., including a sterile filter. The nozzle assembly also includes a spray gas input 1319 for sterile connection to the spray gas source 1320 (e.g., as shown, a nitrogen). In some embodiments, the spray gas connection includes a sterile filter.

The attachment 1301 also includes a drying chamber 1310, a collection device 1311, and a storage container 1312. As in the spray drying systems above, plasma, drying gas, and spray gas are combined at a spray nozzle of the nozzle assembly, and sprayed into drying chamber 1310. Dried plasma powder is collected by the collection device 1311 (as shown a cyclone chamber) and transferred to the storage container 1302. The collection device includes a gas output port 1313 which connects back to the main body of the spray drying system 1300 through a sterile filter. Gas from the output port is directed to an air conditioner 1314 which dehumidifies the gas, and circulates the dried gas back to the drying gas source 1305. Waste fluid produced during the dehumidification is directed to a waste fluid storage container 1315

Attachment 1301 includes a sterile isolated spray drying environment which connects to the main body of the spray drying system only through sterile connections. Accordingly, after a spray drying run, a fresh isolated sterile spray drying environment can be obtained by simply removing the attachment 1301 and replacing it with a unused attachment. The new attachment 1301 need only be connected to the main body of the system 1300, and nothing on the main body of the system 1301 requires sterilization. Accordingly, the system 1301 can be quickly changed over between spray drying runs, allowing for the efficient production of dried plasma powder.

One or more portions of the attachment 1301 may be collapsible for efficient storage. For example, in some embodiments, the drying chamber 1310 is collapsible, e.g., in an accordion fashion. One or more portion of attachment 1301 may be made of a plastic or polymer material, or other suitable material (e.g., chosen for light weight, low cost, ease of fabrication, etc.).

In some embodiments, system 1300 includes a mechanism for positively identifying the attachment 1301 as an appropriate attachment for the system. The mechanism may include a bar code reader, an RFID system, etc. In one embodiment, the attachment 1310 includes a microchip that stores an encrypted code which is read by the system 1300 to verify the identity of the attachment 1301.

In some embodiments, system 1300 includes one or more sensors, interlocks, etc., to confirm the proper attachment of the attachment 1301. In some embodiments, the sensors are in communication with a controller which prevents operation of the system 1300 in the event of improper or incomplete attachment.

As shown, spray dry system 1300 includes a device 1316 for automatic sealing and removal of the storage container 1312. The device 1316 may include an automated clamping and cutting mechanism, to seal of the container 1312 and remove it from the attachment 1301.

Figure 14A:
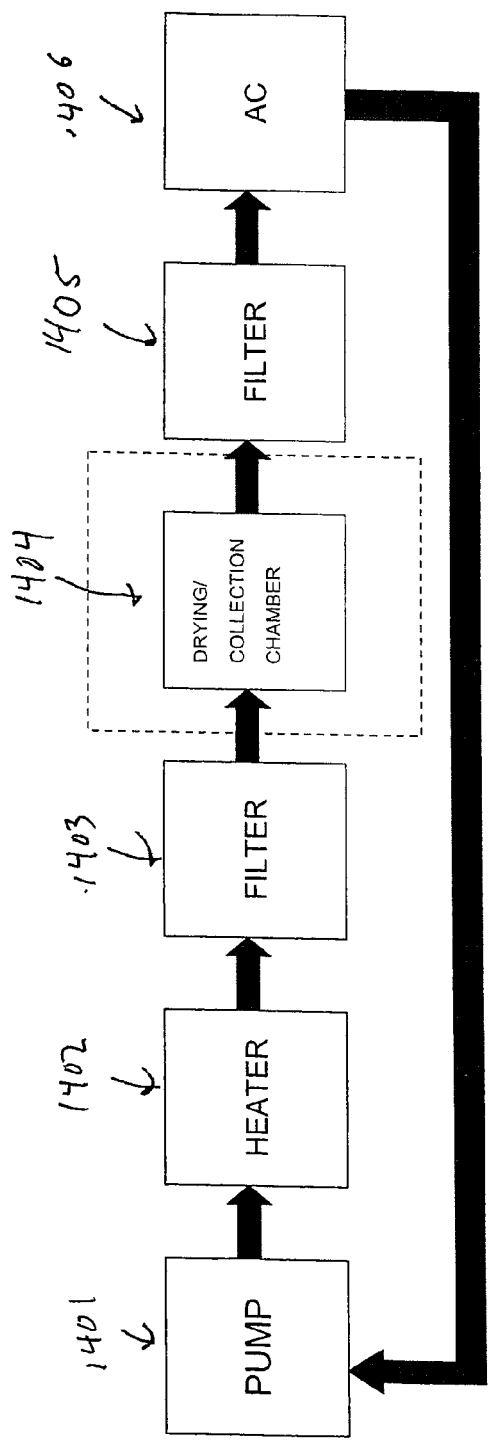

FIGS. 14A-14D illustrate various air flow configurations for the spray dry systems of the types described herein. Referring to FIG. 14A, in one embodiment, a pump 1401 receives dry air and directs a stream of dry air to heater 1402 for heating. The heated dry air passes through sterile filter 1403, and through a spray nozzle (not shown) into a sterile, isolated drying and particle collection chamber 1404. The air stream is output through a second filter 1405 to an air conditioning unit 1406 for dehumidification. Dry air from the air conditioning unit 1406 is drawn in to pump 1401 to begin the cycle again. Accordingly, the air stream is recirculated in a closed loop fashion.

Figure 14B:
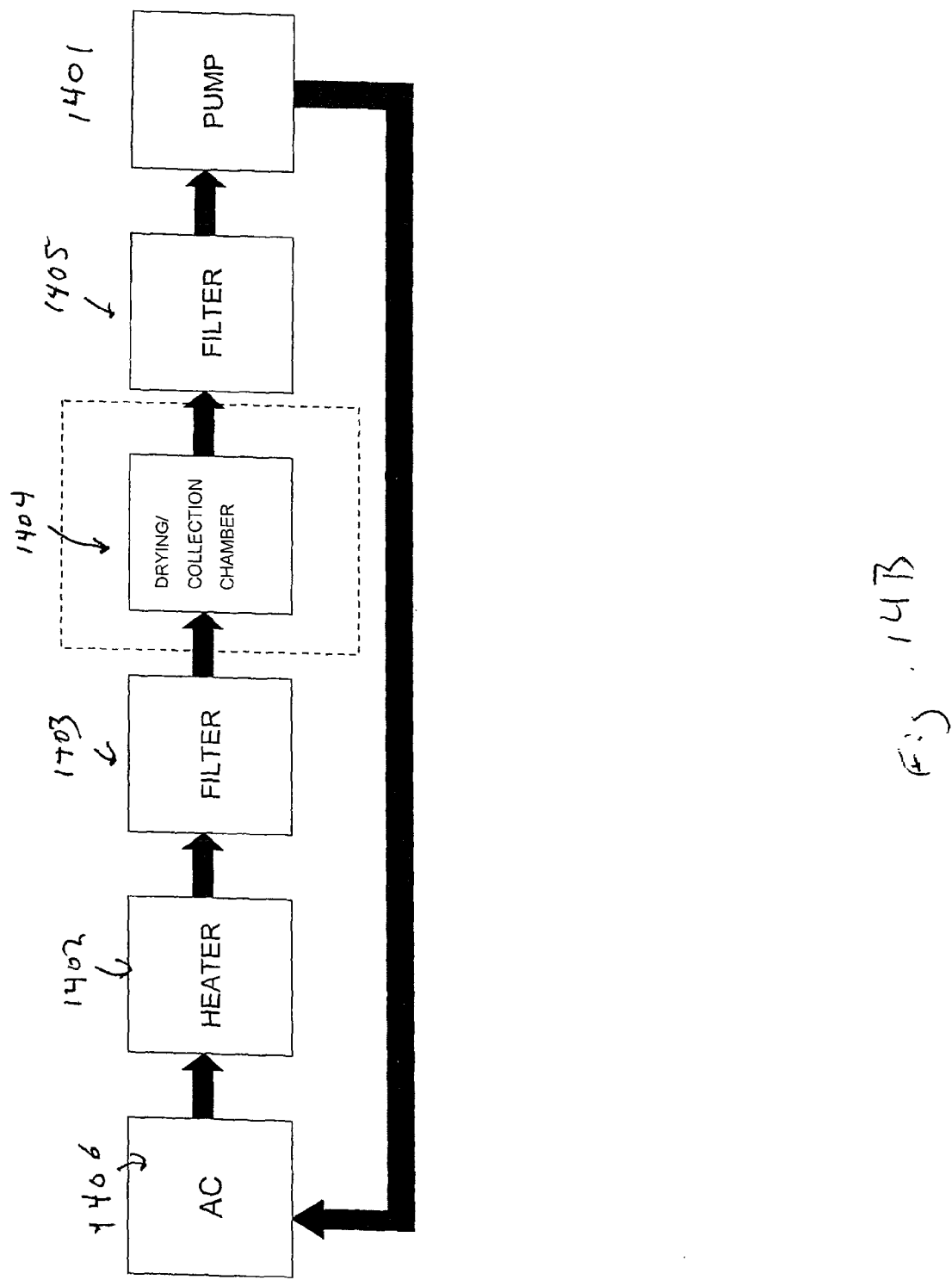
Figure 14C:
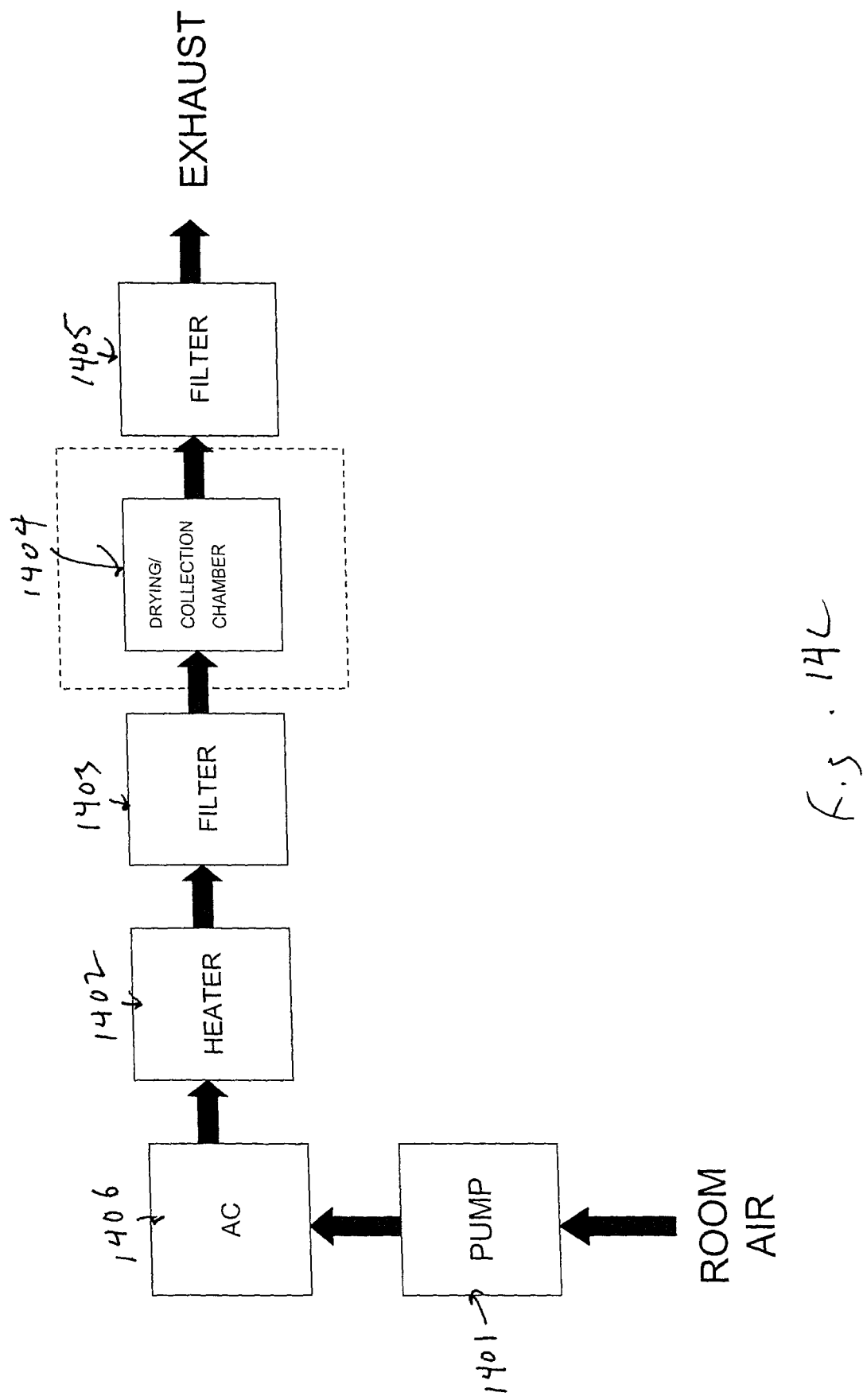
Figure 14D:
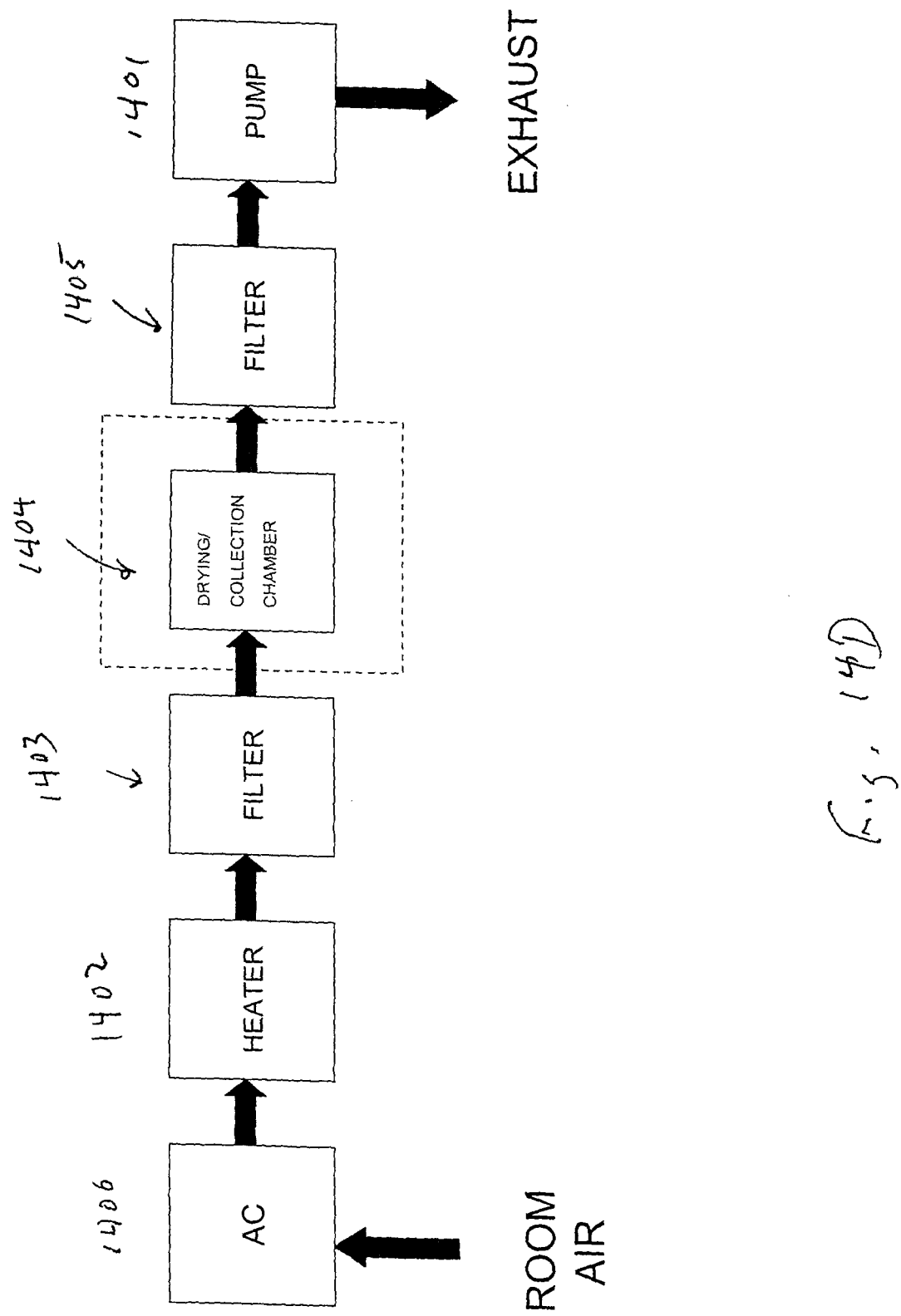

Referring to FIG. 14B, in another embodiments, the pump 1401 is located on the output side of drying and collection chamber 1404. The pump 1401 draws air out of the chamber 1404 through the filter 1405, and directs the air stream to the air conditioning unit 1406 for dehumidification. Dry air from the air conditioning unit 1406 is directed through the heater 1402 and through the filter 1403 into the drying and collection chamber 1404. Accordingly, the air stream in recirculated in a closed loop fashion.

Referring to FIG. 14C, in another embodiment, the air stream is not recirculated in a closed loop. The pump 1401 draws in room air, and directs an air stream to the air conditioning unit 1406 for dehumidification. Dry air from the air conditioning unit 1406 is directed through the heater 1402 and through the filter 1403 into the drying and collection chamber 1404. Air output from the chamber 1404 passes through the filter 1405 and is exhausted to an external environment.

Referring to FIG. 14D, in another embodiment, the air stream is again not recirculated in a closed loop. In this case, the pump 1401 is located on the output side of the drying and collection chamber 1404. The pump 1401 provides negative pressure which draws room air into the air conditioning unit 1406 for dehumidification. Dry air from the air conditioning unit 1406 is directed through the heater 1402 and through the filter 1403 into the drying and collection chamber 1404. Air is drawn out through the filter 1405 to the pump 1401, and is exhausted to an external environment.

Note that in each of the configurations shown in FIGS. 14A-14D, the air stream passes into and out of the drying and collection chamber 1404 through sterile filters. Accordingly, the chamber is maintained as an isolated sterile environment (as indicated by the dotted box). This is the case both for the closed loop recirculating configurations shown in FIGS. 14A-14B, and the open non circulating air stream configurations shown in FIGS. 14C-14D.

In various embodiments, spray drying systems as described herein produce waste fluid as a byproduct of the drying process. In some embodiments (e.g., in the system shown in FIG. 13A), the waste fluid is collected in a detachable receptacle, which can be discarded using the standard protocols for disposal of biomedical waste. In some embodiments, the spray drying system may be connected (e.g., hard or soft plumbed) to a treatment facility which receives and treats waste fluid from the system. In some embodiments, the spray drying system may include one or more waste treatment devices for treating the waste fluid. For example, the system may include a reservoir of treatment material (e.g., chlorine bleach), which may be mixed with the waste fluid to render it safe for disposal in a standard sewer system. In some such embodiments, the system may be connected (e.g., hard or soft plumbed) to the sewer system.

In various embodiments, the spray drying systems as described herein may include a process tracking and management capability. For example, in some embodiments, the system may include a device (e.g., bar code reader, RFID reader, etc.) that reads information. The information may include the identity, type, lot, etc. of plasma units input into the system, the identity, type, lot, etc of output dried plasma powder units, etc. This information may be processed and/or recorded using a processor (e.g., a general purpose computer) and/or a memory (e.g., a hard drive). The system may include a device (e.g., a printer) for marking input plasma or output dry plasma units with identifying information.

In various embodiments, spray drying systems as described herein may be connected, e.g., via a local area network, wide area network, the internet, etc.) to one or more external systems, databases, etc. For example the spray drying system may communicate with one or more computer systems or databases of blood centers for the purpose of process tracking and management. In some embodiments, the operation of the spray drying system may be controlled remotely. For example, in some applications, the spray drying system could be switched on or off or otherwise controlled in response to information regarding the current local need for plasma products.

Figure 8A:
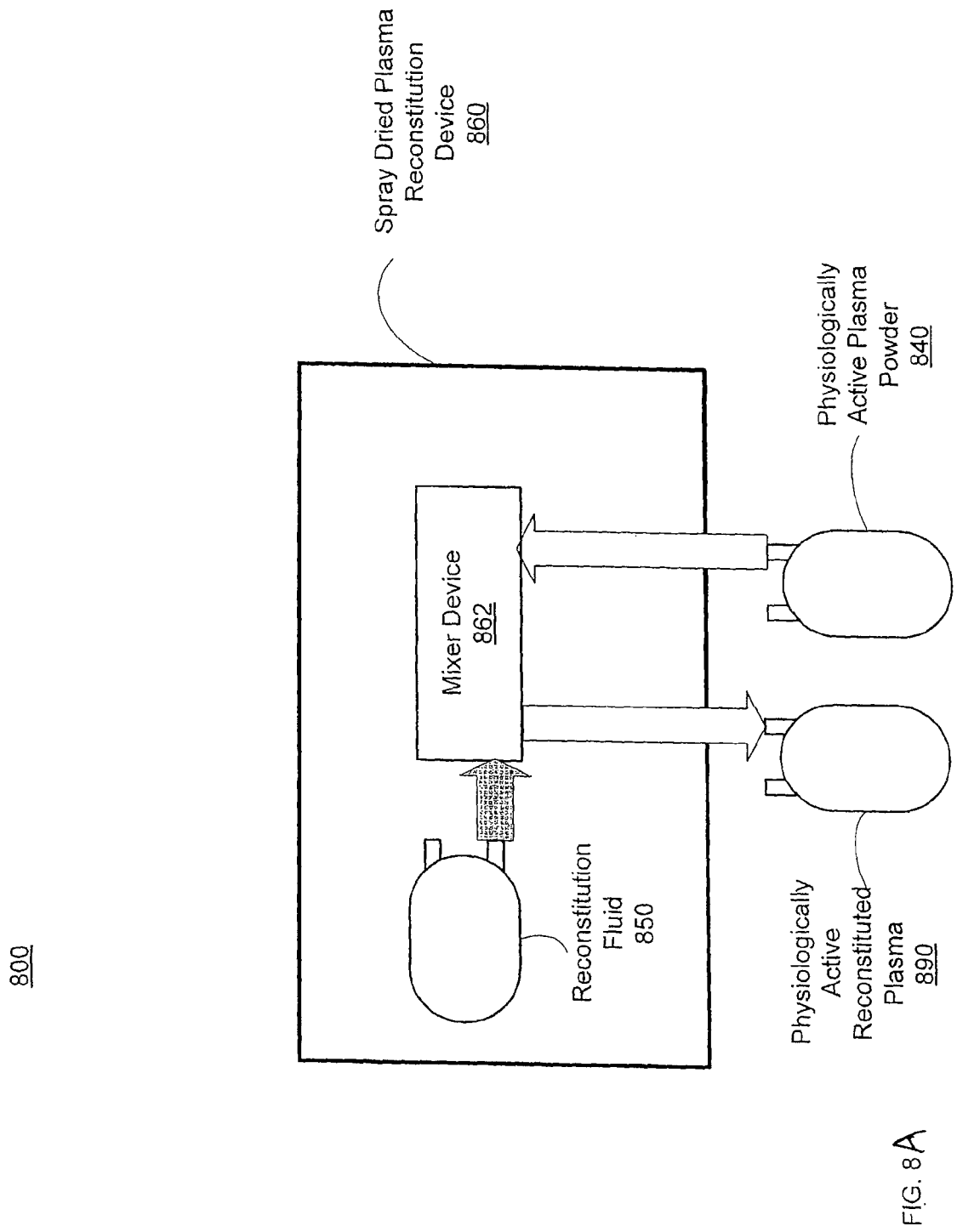

FIG. 8A is a diagram of an exemplary spray dried plasma reconstitution device 860 in reconstitution system 800. The system 800 includes physiologically active plasma powder 840, the spray dried plasma reconstitution device 860, and physiologically active reconstituted plasma 890. The spray dried plasma reconstitution device 860 includes reconstitution fluid 850 and a mixer device 862 (e.g., agitation device, mixing blades, etc.).

The physiologically active plasma powder 840 and the reconstitution fluid 850 is provided to the mixer device 862. The mixer device 862 mixes (e.g., rocking, agitation, physical movement, blades, shaking, vibration, etc.) the physiologically active plasma powder 840 and the reconstitution fluid 850 (e.g., 100 mL, 200 mL, 300 mL, 400 mL, 500 mL, 600 mL, 700 mL, 800 mL, 900 mL, 1000 mL, etc.) to form the physiologically active reconstituted plasma 890. The mixer device 862 can mix the physiologically active plasma powder 840 and the reconstitution fluid 850 for a predefined (e.g., thirty seconds, two minutes, etc.) and/or a variable time period (e.g., variable time period based on an optical sensor that measures the mixing of the substances, etc.).

In some embodiments, the physiologically active plasma powder 840 and/or the reconstitution fluid 850 are connected to the spray dried plasma reconstitution device 860 via a permanent and/or a reusable connection (e.g., syringe connection, standard medical connection, a luer taper connection, twist and lock connection, one time use connection, etc.).

Figure 8B:
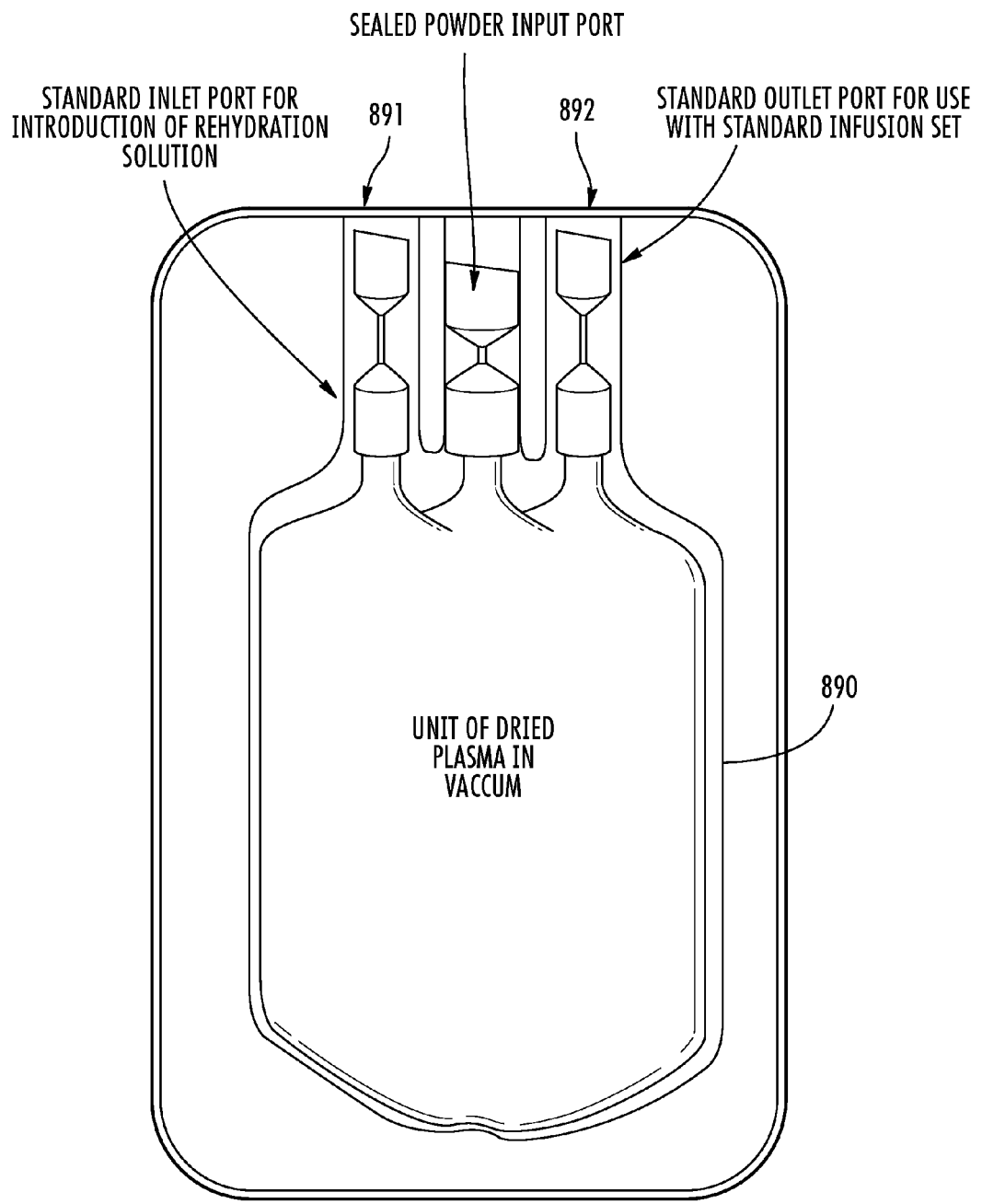

In other embodiments, the mixer device 862 transfers the reconstitution fluid 850 into the bag with the physiologically active plasma powder 840. The bag with the physiologically active plasma powder 840 can be large enough to include both the physiologically active plasma powder 840 and the reconstitution fluid 850. In a further embodiment, the spray dried plasma reconstitution device can be a syringe with a nozzle (or other fluid input device) that injects the reconstitution fluid into the bag with the physiologically active plasma powder 840. In this embodiment, the bag with the physiologically active plasma powder 840 and the reconstitution fluid 850 can be rocked (manually or automatically), e.g., for thirty seconds to two minutes to mix the powder 840 and the fluid 850 together to form the physiologically active reconstituted plasma 890. As shown in FIG. 8B, a dry plasma powder storage 890 bag may be provided which includes standard input and output connectors 891 and 892 to facilitate introduction of reconstitution fluid, and output of reconstituted plasma e.g., to a standard transfusion set.

FIG. 9A is a diagram of an exemplary integrated storage and reconstitution device 900. The device 900 includes a spray dried plasma storage device 950, a spray dried plasma reconstitution device 960, a sealing mechanism 955, and a reconstitution device 957. The spray dried plasma storage device 950 includes physiologically active plasma powder 952. The dried plasma reconstitution device 960 includes reconstitution fluid 965.

The sealing mechanism 955 (e.g., plastic seal, ceramic seal, polymer seal, inter lockable connections, etc.) separates the physiologically active plasma powder 952 and the reconstitution fluid 965 from mixing before the user and/or the automated control system needs the components mixed. The user and/or the automated control system releases the sealing mechanism 955 to release the physiologically active plasma powder 952 and the reconstitution fluid 965 to the reconstitution device 957. The reconstitution device 957 reconstitutes physiologically active reconstituted plasma 990 from the physiologically active plasma powder 952 and the reconstitution fluid 965.

Figure 9B:
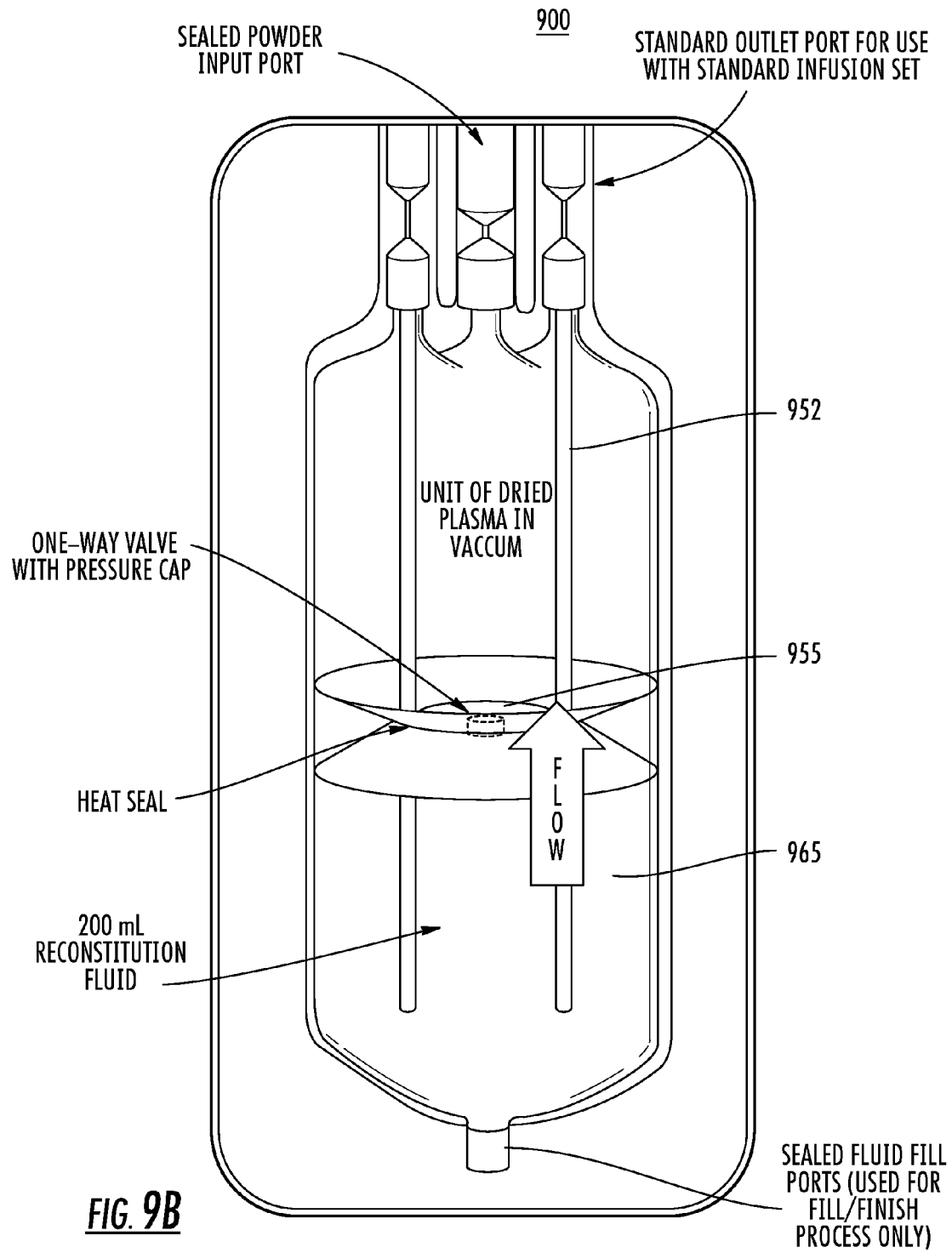

In some embodiments, e.g., as shown in FIG. 9B the integrated storage and reconstitution device 900 is a flexible, plastic container and the physiologically active plasma powder 952 and the reconstitution fluid 965 are each stored in a sub compartment of the plastic container. In this embodiment, the sealing mechanism 955 forms a seal between the two sub compartments. Upon release of the sealing mechanism 955, the physiologically active plasma powder 952 and the reconstitution fluid 965 mix together. In some embodiments, the reconstitution device 957 includes fins within the integrated storage and reconstitution device 900 that mix the physiologically active plasma powder 952 and the reconstitution fluid 965 together upon movement of the device 900 (e.g., shaking by the user, centrifuge by the automated control system, etc.).

FIG. 10 is a flowchart 1000 depicting an exemplary spray drying process for plasma. A user and/or an automated control system warms up (1005) the spray drying apparatus 240 of FIG. 2 (e.g., pre heats the air stream, pressurizes the apparatus via the vacuum device or pump, etc.). The user and/or the automated control system starts (1010) the spray drying apparatus 240. The plasma 210 is provided (1020) to the spray drying apparatus 240. The user and/or the automated control system sets (1030) one or more parameters of the spray drying apparatus 240 (e.g., inlet temperature, outlet temperature, etc.). The user and/or the automated control system starts (1040) the spray drying process. The user and/or the automated control system collects (1050) the physiologically active plasma powder 290 from the spray drying apparatus 240.

FIG. 11 is a flowchart 1100 depicting another exemplary spray drying process for plasma. A user and/or an automated control system attaches (1110) the dehumidifier 344 to the spray drying apparatus 340 of FIG. 3. The user and/or the automated control system attaches (1115) a pre dryer to the spray drying apparatus 340, e.g., to pre heat air input to heated air supply 344 (e.g., using hot air output from a dehumidifier or other component of the system). For spray drying systems which do not use pre heating, this step may be omitted.

The user and/or the automated control system attaches (1120) glassware (e.g., the drying chamber 352, the cyclone chamber 356, the powder collection chamber 358, etc.) to the spray drying apparatus 340. Alternatively, as described in reference to FIGS. 13A-13E, a disposable attachment may be used.

The user and/or the automated control system sets (1125) the inlet temperature to a desired value on the spray drying apparatus 340. The inlet temperature can be, for example, the temperature of the air stream entering the nozzle 348. In other embodiments, the inlet temperature is the temperature of the atomized plasma as it enters the drying chamber 350. In some embodiments the inlet temperature is set to about 112° C. In various embodiments, any suitable inlet temperature may be used, e.g., an inlet temperature in the range of 85-150° C., or in the range of 100-120° C., or in the range of 110-115° C., etc.

The user and/or the automated control system sets (1130) the pump rate for the peristaltic pump 342 to a desired value. In some embodiments the pump rate is set to about 9 mL/minute. In various embodiments, any suitable pump rate may be used, e.g., a pump rate in the range of 3-14 mL/minute, or in the range of 7-11 mL/minute, or in the range of 8-10 mL/minute, etc.

The user and/or the automated control system sets (1135) the aspiration of the vacuum supply or drying gas pump to provide a flow rate out of the collection device 358 to 35 m³/hour. In various embodiments, any suitable flow rate may be used, e.g., a flow rate in the range of 25-80 m³/hour, or in the range of 30-40 m³/hour, or in the range of 33-37 m³/hour, etc.

The user and/or the automated control system sets (1140) the flow rate from the non reactive spray gas supply 346 to a desired value, e.g., 414 L/hour. In various embodiments, any suitable flow rate may be used, e.g., a flow rate in the range of 300-500 L/hour, or in the range of 350-450 L/hour, or in the range of 375-425 L/hour, etc.

The user and/or the automated control system starts (1145) the spray drying process on the spray drying apparatus 340. The user and/or the automated control system collects (1160) the physiologically active plasma powder 390.

During the processing of the plasma 310 by the spray drying apparatus 340, an output optimization device (e.g., 261 of FIG. 2) monitors (1150) the outlet temperature of the physiologically active plasma powder 390 at the powder collection chamber 358 (or other suitable position) via the outlet temperature device 354. If the outlet temperature is substantially outside of the range of 40° C. to 44° C., the output optimization device adjusts (1155) the pump rate and/or the inlet temperature to correct the output temperature. Table 1 illustrates exemplary output temperatures and adjustments to the pump rate and/or the inlet temperature.

TABLE 1

Exemplary Outlet Temperatures and Respective Adjustments.

| Outlet Temperature | Set Pump Rate (mL/min) | Pump Rate Adjustment (mL/min) | Set Inlet Temperature | Inlet Temperature Adjustment |
|---|---|---|---|---|
| 38° C. | 11.5 | −2 | 107° C. | — |
| 39° C. | 11.5 | — | 107° C. | +4° C. |
| 48° C. | 11.5 | +1 | 107° C. | −1° C. |
| 45° C. | 11.5 | — | 107° C. | −2° C. |

In general, in various embodiments, the spray drying systems described herein may feature open or closed loop control of one or more process parameters. One or more sensors (e.g., temperature sensors, flow rate sensors, pressure sensors, etc.) may be used to monitor the process. Information from these sensors (either alone or in combination) can be processed and used to control one or more process parameter (e.g., plasma flow rate, drying gas flow rate, spray gas flow rate, drying gas inlet temperature, etc.). For example, a closed servo loop may be used to control one or more sensed process parameters (e.g., drying gas outlet temperature, plasma flow rate, drying gas flow rate, spray gas flow rate, drying gas inlet temperature, etc.) at a desired value or range of values by adjusting one or more other process parameters. Process control may be implemented using any techniques known in the art, e.g., in software (e.g., run on a general purpose computer), hardware, or a combination thereof. For example, various embodiments feature closed servo loop control of the spray drying outlet temperature at a desired value (e.g., 42° C.) or range of values (e.g., 41-43° C., less than 43° C., etc.) by adjusting, e.g., the plasma pump rate, the drying gas inlet temperature, or a combination thereof. The servo loop may be implemented using any techniques know in the art, e.g., in software (e.g., run on a general purpose computer), hardware, or a combination thereof.

Figure 12:
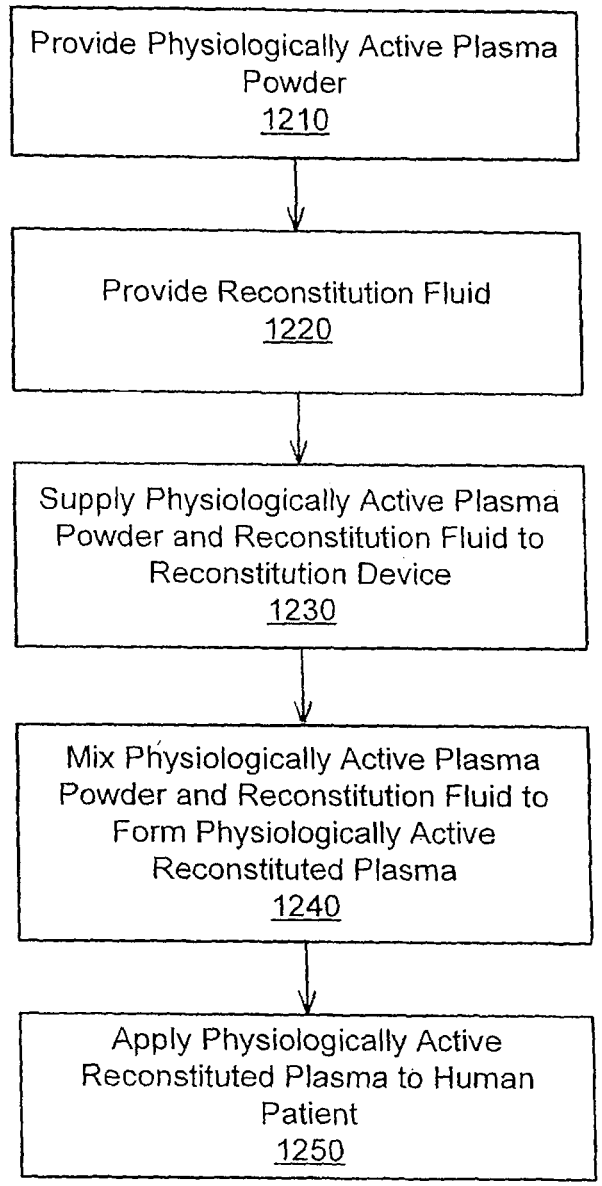

FIG. 12 is a flowchart 1200 depicting an exemplary process of applying physiologically active reconstituted plasma to a human patient utilizing the integrated storage and reconstitution device 900 of FIG. 9. The integrated storage and reconstitution device 900 provides (1210) the physiologically active plasma powder 952. The integrated storage and reconstitution device 900 provides (1220) the reconstitution fluid 965. The sealing mechanism 955 supplies (1230) the physiologically active plasma powder 952 and the reconstitution fluid 965 to the reconstitution device 957. The reconstitution device 957 mixes (1240) the physiologically active plasma powder 952 and the reconstitution fluid 965 to form the physiologically active reconstituted plasma 990. A user and/or an automated control system applies (1250) the physiologically active reconstituted plasma 990 to a human patient (e.g., the user, a medical user, etc.).

In some embodiments, the plasma described herein is human plasma. The plasma can be, for example, diluted (e.g., glycine, water, blood thinner, etc.) and/or undiluted (e.g., undiluted plasma separated from the blood).

In other embodiments, the parameters utilized for the spray drying apparatus are illustrated in Table 2.

TABLE 2

Parameters for Spray drying Apparatus

| Parameter | Setting | Range A | Range B |
|---|---|---|---|
| Inlet Temperature | 107° C. | 100° C. to 114° C. | 102° C. to 112° C. |
| Pump Setting (mL/min) | 11.5 | 7.1 to 14.4 | 9.5 to 12.0 |

TABLE 2-continued

Parameters for Spray drying Apparatus

| Parameter | Setting | Range A | Range B |
|---|---|---|---|
| Aspiration (m³/hr) | 35 | 20 to 35 | 30 to 35 |
| Spray Flow Rate (Nitrogen) (L/hr) | 414 | 360 to 475 | 340 to 445 |
| Outlet Temperature (Monitor) | NA | 40° C. to 44° C. | 42° C. to 43° C. |

In other embodiments, the parameters utilized for the spray drying apparatus can be varied as illustrated in Table 3.

TABLE 3

Parameters for Spray drying Apparatus

| Parameter | Settings A | Settings B | Settings C |
|---|---|---|---|
| Inlet Temperature | 101-113° C. | 96-118° C. | 85-129° C. |
| Pump Setting (mL/min) | 9.8-12.0 | 9.0-13.0 | 18.0-15.0 |
| Aspiration (m³/hr) | 30-35 | 28-35 | 20-35 |
| Spray Flow Rate (Nitrogen) (L/hr) | 390-445 | 365-450 | 325-500 |
| Outlet Temperature (Monitor) | 38-46° C. | 36-48.4° C. | 32-61.6° C. |

In some embodiments, (e.g., using diluted plasma) the parameters utilized for the spray drying apparatus are dependent on the protein concentration of the plasma. In other words, the parameters change based on the amount of protein per volume of the plasma. For example, in some embodiments, at 10 mg of protein per 100 ml of volume, the inlet temperature setting is 107° C. As another example, in some embodiments, at 25 mg of protein per 100 ml of volume, the inlet temperature setting is 109° C.

In some embodiments, the plasma 310 is cooled (or heated) before being pumped into the spray drying apparatus 340 by the peristaltic feed pump 342. In this example, the bag of plasma can be cooled before being connected to the spray drying apparatus 340.

In other embodiments, the human plasma is collected by apheresis. The human plasma can be dried and tested using the spray dry method described herein.

In some examples, the spray drying apparatus is setup per the parameters and/or steps described below. Although the following steps are numbered sequentially, the steps can occur in any order. The Buchi equipment and/or parts described herein are available from BÜCHI Labortechnik AG of Flawil, Switzerland.

1. Provide 200 ml frozen bag of plasma collected by apheresis
2. Thaw the frozen bag of plasma in a 38° C. water bath
3. Provide the Buchi B 290 spray dryer
4. Attach the Buchi B 296 dehumidifier to the spray dryer, for example, according to Buchi instructions
5. Attach Buchi pre dryer heat exchanger to the spray dryer, for example, according to Buchi instructions
6. Attach Buchi outlet HEPA filter to the spray dryer
7. Check that all glassware components are clean and dry
8. Attach Buchi high volume glassware set to the spray dryer according to Buchi instructions
9. Empty receiving bottle of Buchi B 296 dehumidifier
10. Attach thawed bag of plasma to the Buchi B 290 spray dryer
11. Set inlet temperature range of spray dryer to 107° C.
12. Set pump setting to 11.5 mL/minute (in other examples, the pump setting is set in a range from 7.1 to 14.4 mL/minute)
13. Set aspiration to 35 m³/hr
14. Set non reactive gas (e.g., nitrogen) flow rate to 360-475 L/hour depending on flow rate
15. Monitor outlet temperature and adjust pump rate (e.g., first adjustment) and inlet temperature (e.g., second adjustment) to keep the outlet temperature between 40-44° C.

Figure 16D:
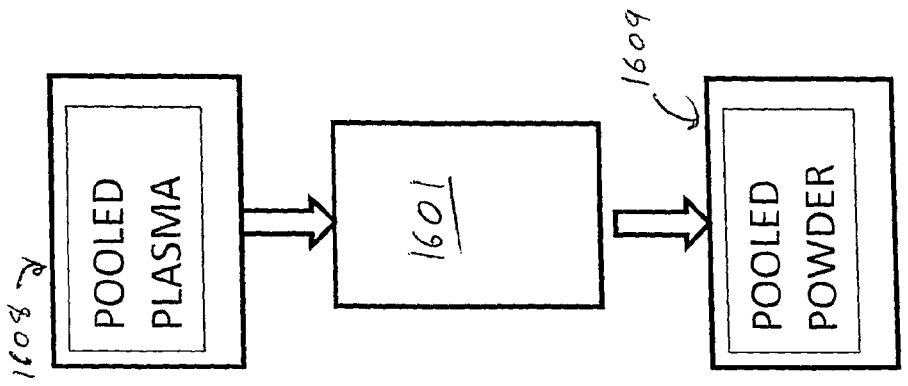
FIGS. 16A-16D are diagrams illustrating spray dry batch process procedures.
Figure 16C:
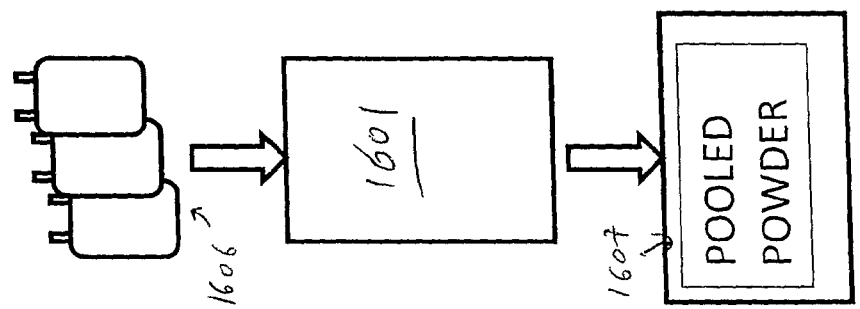

Plasma spray drying systems of the type described herein provide for closed sterile processing of plasma into a dried plasma product. For example, referring to FIG. 16A, in some embodiments, the spray drying system 1601 receives a single unit of plasma 1602. The plasma is processed under closed sterile conditions to produce a single unit of dried plasma in a closed sterile container 1603. The closed sterile container 1603 may be sealed and removed for closed sterile storage. Such processing may be referred to as unit to unit processing.

Figure 16B:
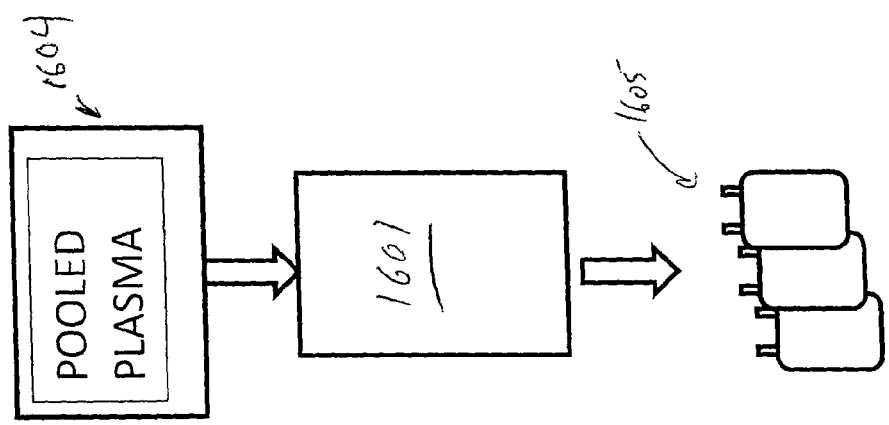
Figure 16A:
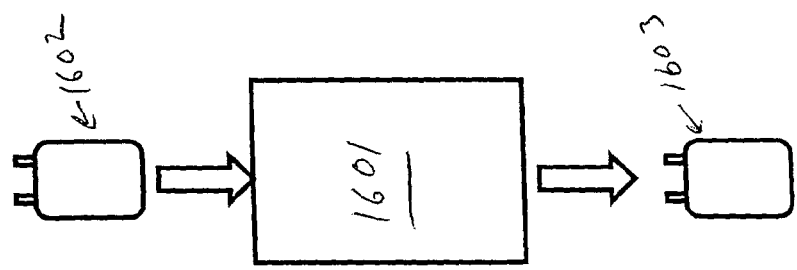

Referring to FIG. 16B, in some embodiments, the spray drying system 1601 receives plasma from a pool of plasma 1604 (e.g., collected from multiple donors). The plasma is processed under closed sterile conditions to produce one or more single units of dried plasma, each in a closed sterile container 1605. For example, plasma from the pool 1604 may be processed until a first unit of dried plasma is produced and stored in a single storage container 1605. The storage container 1605 can then be sealed and removed from the spray dry system 1601 for closed sterile storage. A new empty sterile storage bag 1605 is attached to the spray dry 1601 system without compromising the closed environment of the system, and the process is repeated. Such processing may be referred to as pool to unit processing.

Referring to FIG. 16C, in some embodiments, the spray drying system 1601 receives multiple single units of plasma 1606 (e.g., collected from multiple donors) either in sequence or in parallel. The plasma is processed under closed sterile conditions to produce a pool of multiple units of dried plasma in a single closed sterile storage container 1607. For example, a first unit of plasma 1606 may be attached to the spray drying system without compromising the closed sterile environment of the spray dry system 1601. The unit 1606 is processed, and dried plasma powder collected in the storage container 1607. Once processing of the first unit 1606 is complete, the unit 1606 and/or the storage container 1607 is removed without compromising the closed sterile environment of the spray dry system 1601. A new unit of plasma 1606 is attached to the spray drying system 1601 while maintaining the closed sterile environment of the system, and the process repeated. Once spray dried plasma powder from several plasma units 1606 has been collected in the storage container 1607, the storage container 1607 is sealed and removed for closed sterile storage. Such processing may be referred to as pool to unit processing.

Referring to FIG. 16D, in some embodiments, the spray drying system 1601 receives plasma from a pool of plasma 1608 (e.g., collected from multiple donors). The plasma is processed under closed sterile conditions to produce a pool of multiple units of dried plasma in a single closed sterile storage container 1609. For example, a volume of plasma equivalent to multiple units is delivered from the pool 1608 for processed under closed sterile conditions. The resulting dried plasma powder is stored in a single storage container 1605. After a desired amount of powder is collected, the storage container 1609 can then be sealed and removed from the spray dry system 1601 for closed sterile storage. Such processing may be referred to as pool to pool processing.

In various embodiments, a single spray drying system may operate in multiple modes corresponding to some or all of the above described processing schemes (unit to unit, pool to unit, unit to pool, pool to pool, etc.). Advantageously, such systems may switch between modes without requiring substantial reconfiguration of the system.

EXAMPLE I

Table 4 illustrates test results between fresh frozen plasma, spray dried plasma rehydrated with 2 mL of water, and spray dried plasma powder rehydrated with 2 mL of glycine. The text results were obtained using a STart® 4 semi automated homostasis analyzer available from Diagnostica Stago, Inc. of Parsippany, N.J. Note that the Factor V and Factor VII values of the FFP are presented as a clotting time value with units of seconds, and not as an absolute level in units of IU/dL.

TABLE 4

Spray dried Plasma vs. Fresh Frozen Plasma

| | Total Protein (mg/mL) | Percentage of Protein Compared to Fresh Frozen Plasma | Prothrombin Time (PT) (sec) | Factor V (sec) | Factor VII (sec) |
|---|---|---|---|---|---|
| Fresh Frozen Plasma | | | | | |
| | 50 | NA | 15 | 15 | 16 |
| Spray Dried Plasma rehydrated with 2 mL water | | | | | |
| 100 mg | 31 | 61% | 18 | 18 | 16 |
| 200 mg | 56 | 111% | 16 | 16 | 16 |
| 300 mg | 78 | 155% | 19 | 20 | 19 |
| Spray Dried Plasma rehydrated with 2 mL glycine | | | | | |
| 100 mg | 35 | 69% | 18 | 16 | 16 |
| 200 mg | 61 | 121% | 15 | 15 | 16 |
| 300 mg | 82 | 163% | 16 | 16 | 16 |
| 400 mg | 97 | 193% | 18 | 17 | 17 |

EXAMPLE II

FIG. 17A shows a chart which illustrates the results of tests on spray dried plasma samples. Fresh plasma (<24 hour from draw) was dried under varying processing conditions. A first set of dried plasma units was dried with an inlet temperature of 97° C. and a fixed plasma flow rate of 3 mL/min. A second set was dried with a drying gas inlet temperature of 97° C. and with a plasma flow rate which was varied to maintain a desired gas outlet temperature. A third set was dried with a drying gas inlet temperature of 112° C. and with a plasma flow rate which was varied to maintain a desired gas outlet temperature. A fourth set was dried with a drying gas inlet temperature of 117° C. and with a plasma flow rate which was varied to maintain a desired gas outlet temperature.

A sample from each of the dried units was reconstituted in deionized water (e.g., at a ratio of 0.09 g of powder per mL of deionized water). The reconstituted plasma was tested with a Stago Compact series analyzer available from available from Diagnostica Stago, Inc. of Parsippany, N.J. The samples were tested for PT, aPTT, Fibrinogen Level, levels of Factors V, VII, VIII, and IX, Protein C level, and Protein S level. The results are presented in FIG. 17A.

FIG. 17B shows a chart which illustrates the results of tests on spray dried plasma samples. Fresh plasma (<24 hour from draw) was dried under varying processing conditions. The samples were run at various inlet temperatures ranging from 97-112° C. (batches labeled 2010-102 and 2010-104 at 97° C.; batches labeled 2010-040 through 2010-074 at 112° C., and batches labeled 2010-081 and 2010-083 at 117° C.). In each case, the plasma flow was varied to maintain a desired gas outlet temperature.

Each sample was reconstituted using a glycine solution (e.g., at a ratio of 0.09 g of powder per mL of reconstitution fluid). The reconstituted plasma was tested with a Stago STA series analyzer available from available from Diagnostica Stago, Inc. of Parsippany, N.J. The samples were tested for PT, aPTT, Fibrinogen Level, levels of Factors V, VII, VIII, and IX, Protein C level, and Protein S level. The results are presented in FIG. 17B.

DEFINITIONS aPTT—Activated Partial Thromboplastin Time is a performance indicator known in the art measuring the efficacy of both the "intrinsic" (sometimes referred to as the contact activation pathway) and the common coagulation pathways.

PT—Prothrombin Time is a performance indicator known in the art of the extrinsic pathway of coagulation.

FGN—Fibrinogen (also referred to in the art as Factor I) is an asoluble plasma glycoprotein, synthesized by the liver, that is converted by thrombin into fibrin during coagulation.

PC—Protein C is also known as autoprothrombin IIA and blood coagulation Factor XIV, is an inactive protein, the activated form of which plays an important role in managing blood clotting, inflammation, cell death and the permeability of blood vessel walls in humans and other animals.

PS—Protein S is a vitamin K-dependent plasma glycoprotein synthesized in the endothelium. In the circulation, Protein S exists in two forms: a free form and a complex form bound to complement protein C4b. In humans, protein S is encoded by the PROS1 gene. The best characterized function of Protein S is its role in the anti coagulation pathway, where it functions as a cofactor to Protein C in the inactivation of Factors Va and VIIIa. Only the free form has cofactor activity.

Factors—As used here a "Factor" followed by a Roman Numeral refers to a series of plasma proteins which are related through a complex cascade of enzyme-catalyzed reactions involving the sequential cleavage of large protein molecules to produce peptides, each of which converts an inactive zymogen precursor into an active enzyme leading to the formation of a fibrin clot. They include: Factor I (fibrinogen), Factor II (prothrombin), Factor III (tissue thromboplastin), Factor IV (calcium), Factor V (proaccelerin), Factor VI (no longer considered active in hemostasis), Factor VII (proconvertin), Factor VIII (antihemophilic factor), Factor IX (plasma thromboplastin component; Christmas factor), Factor X (Stuart factor), Factor XI (plasma thromboplastin antecedent), Factor XII (hageman factor), and Factor XIII (fibrin stabilizing factor).

Although the methods and apparatuses described herein are described as processing/utilizing plasma, the method and apparatuses described herein can, for example, be utilized to process/utilize any type of blood product (e.g., whole blood, blood platelets, red blood cells, blood serum, etc.).

Comprise, include, and/or plural forms of each are open ended and include the listed parts and can include additional parts that are not listed. And/or is open ended and includes one or more of the listed parts and combinations of the listed parts.

One or more documents are incorporated by reference in the current application. In the event that the meaning of a technical term in an incorporated document conflicts with the current application, the meaning in the current application is controlling.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. An attachment for a plasma spray drying apparatus comprising:
   a plasma inlet port for providing sterile communication to a plasma source;
   a spray gas inlet port for providing removable sterile communication to a pressurized gas source;
   at least one drying gas inlet port for providing removable sterile communication to a drying gas source;
   a spray dry nozzle in fluid communication with the plasma and spray gas inlets;
   a drying chamber in fluid communication with the attached spray nozzle and drying gas inlet to receive a spray of plasma for drying;
   a particle collection device configured to collect spray dried plasma from an outlet of the drying chamber; and
   a collection device gas outlet port in sterile fluid communication with the collection device;
   wherein the spray nozzle, drying chamber, and collection device define a sterile isolated interior volume.

2. The attachment of claim 1, wherein the attachment comprises a sterile isolated spray drying environment.

3. The attachment of claim 1, wherein at least one of the inlet and outlet ports comprises a sterile filter.

4. The attachment of claim 1, wherein at least one of the drying chamber and the particle collection device is at least partially collapsible.

5. The attachment of claim 1, wherein the attachment is at least partially collapsible.

6. The attachment of claim 1, wherein at least part of the attachment is at least partially collapsible in an accordion fashion.

7. The attachment of claim 1, further comprising a mechanism for positively identifying the attachment.

8. The attachment of claim 7, wherein the mechanism for positively identifying the attachment comprises a bar code, a microchip, a radio frequency identification device (RFID), or any combination thereof.

9. The attachment of claim 1, further comprising one or more sensors to confirm proper attachment to the plasma source, the pressurized gas source, the drying gas source, or any combination thereof.

10. The attachment of claim 1, further comprising one or more sensors to monitor the attachment.

11. The attachment of claim 10, wherein the one or more sensors comprise a temperature sensor, a flow rate sensor, a pressure sensor, or any combination thereof.

12. The attachment of claim 1, wherein the particle collection device comprises a closable sterile storage container to store spray dried plasma.

13. The attachment of claim 12, wherein the closable sterile storage container is sealable by a device for automatic sealing of the particle collection device.

14. The attachment of claim 12, wherein the closable sterile storage container sealable by a device for automatic sealing and removal of the particle collection device.

15. The attachment of claim 1, wherein the attachment comprises a plastic or polymer material.

16. The attachment of claim 1, wherein the particle collection device comprises a cyclone chamber.

17. The attachment of claim 1, wherein the drying chamber comprises a cyclone chamber.

18. The attachment of claim 1, wherein the particle collection device comprises a sterile detachable storage portion configured to receive collected spray dried plasma.

19. The attachment of claim 1, wherein the attachment is disposable.

20. The attachment of claim 1, wherein the plasma inlet port comprises a feed tube with a sealed end for sterile attachment to the plasma source.

21. An attachment for a plasma spray drying apparatus comprising:
   a spray nozzle assembly comprising:
      a plasma input for sterile communication to a plasma source,
      a drying gas input for sterile communication to a drying gas source,
      a spray gas input for sterile communication to a spray gas source, and
      a spray nozzle for combining plasma from the plasma input, a drying gas from the drying gas input, and spray gas from the spray gas input and spraying the combination of the plasma, drying gas, and the spray gas into a drying chamber;
   the drying chamber to dry the sprayed combination of the plasma, drying gas, and the spray gas;
   a collection device to collect dried plasma powder; and
   a storage container to store the collected dried plasma powder.

22. The attachment of claim 21, wherein the attachment comprises a sterile isolated spray drying environment.

23. The attachment of claim 21, wherein the collection device comprises a gas output port to collect gas from the attachment, the gas output port comprises a sterile filter.

* * * * *